(12) United States Patent
Swensgard et al.

(10) Patent No.: US 10,667,812 B2
(45) Date of Patent: Jun. 2, 2020

(54) MODULAR POWERED ELECTRICAL CONNECTION FOR SURGICAL INSTRUMENT WITH FEATURES TO PREVENT ELECTRICAL DISCHARGE

(71) Applicant: ETHICON LLC, Guaynabo, PR (US)

(72) Inventors: Brett E. Swensgard, West Chester, OH (US); Michael D. Auld, Blue Ash, OH (US); Michael J. Vendely, Lebanon, OH (US); Sol Posada, Cincinnati, OH (US); Frederick E. Shelton, IV, Hillsboro, OH (US); David C. Yates, West Chester, OH (US)

(73) Assignee: Ethicon LLC, Guaynabo, PR (US)

( * ) Notice: Subject to any disclaimer, the term of this patent is extended or adjusted under 35 U.S.C. 154(b) by 186 days.

(21) Appl. No.: 15/634,497

(22) Filed: Jun. 27, 2017

(65) Prior Publication Data
US 2018/0368849 A1 Dec. 27, 2018

(51) Int. Cl.
*A61B 17/072* (2006.01)
*A61B 17/00* (2006.01)
(Continued)

(52) U.S. Cl.
CPC .. *A61B 17/07207* (2013.01); *A61B 17/00234* (2013.01); *A61B 17/072* (2013.01);
(Continued)

(58) Field of Classification Search
CPC ...... A61B 17/00234; A61B 2017/0046; A61B 2017/0039; A61B 2017/00022;
(Continued)

(56) References Cited

U.S. PATENT DOCUMENTS

| | | | |
|---|---|---|---|
| 6,783,524 B2 | 8/2004 | Anderson et al. | |
| 7,000,818 B2 * | 2/2006 | Shelton, IV | A61B 17/07207 227/176.1 |

(Continued)

FOREIGN PATENT DOCUMENTS

| | | |
|---|---|---|
| EP | 2 942 016 A1 | 11/2015 |
| EP | 3 061 409 A1 | 8/2016 |
| EP | 3 064 146 A1 | 9/2016 |

OTHER PUBLICATIONS

U.S. Appl. No. 15/634,385, filed Jun. 27, 2017.
(Continued)

*Primary Examiner* — Hemant Desai
*Assistant Examiner* — Jacob A Smith
(74) *Attorney, Agent, or Firm* — Frost Brown Todd LLC

(57) ABSTRACT

An apparatus includes a body assembly, a modular shaft assembly, and a coupling detection assembly. The body assembly includes a control circuit, a battery pack operable to power the control circuit, and a first electrical contact assembly. The modular shaft assembly includes a second electrical contact assembly that is configured to operatively engage the first electrical contact assembly when the modular shaft assembly selectively couples with the body assembly. A detection trigger member is configured to activate a detection activation member such that the detection activation member communicates a first detection signal to the control circuit when the modular shaft assembly selectively couples with the body assembly. The control circuit is configured to verify operative engagement between the first electrical contact and the second electrical contact in response to the control circuit receiving the first detection signal.

20 Claims, 16 Drawing Sheets

(51) Int. Cl.
*A61B 17/115* (2006.01)
*A61B 90/00* (2016.01)

(52) U.S. Cl.
CPC ... *A61B 17/1155* (2013.01); *A61B 2017/0003* (2013.01); *A61B 2017/00022* (2013.01); *A61B 2017/00039* (2013.01); *A61B 2017/0046* (2013.01); *A61B 2017/00057* (2013.01); *A61B 2017/00115* (2013.01); *A61B 2017/00398* (2013.01); *A61B 2017/00464* (2013.01); *A61B 2017/00734* (2013.01); *A61B 2017/07257* (2013.01); *A61B 2090/0808* (2016.02)

(58) Field of Classification Search
CPC .. A61B 2017/0003; A61B 2017/00039; A61B 2017/00115; A61B 2017/00734; A61B 5/7435
USPC .......................................... 227/176.1, 181.1
See application file for complete search history.

(56) References Cited

U.S. PATENT DOCUMENTS

| | | | |
|---|---|---|---|
| 7,380,696 | B2 | 6/2008 | Shelton, IV et al. |
| 7,404,508 | B2 | 7/2008 | Smith et al. |
| 7,434,715 | B2 | 10/2008 | Shelton, IV et al. |
| 7,721,930 | B2 | 5/2010 | McKenna et al. |
| 8,408,439 | B2 | 4/2013 | Huang et al. |
| 8,453,914 | B2 | 6/2013 | Laurent et al. |
| 9,072,535 | B2 | 7/2015 | Shelton, IV et al. |
| 9,186,142 | B2 | 11/2015 | Fanelli et al. |
| 9,351,726 | B2 * | 5/2016 | Leimbach ............. A61B 17/32 |
| 9,717,497 | B2 | 8/2017 | Zerkle et al. |
| 9,795,379 | B2 | 10/2017 | Leimbach et al. |
| 9,808,248 | B2 | 11/2017 | Hoffman |
| 2014/0107640 | A1* | 4/2014 | Yates ................. A61B 18/1482 606/33 |
| 2014/0263541 | A1 | 9/2014 | Leimbach et al. |
| 2014/0305989 | A1* | 10/2014 | Parihar .............. A61B 17/1155 227/176.1 |
| 2015/0053749 | A1* | 2/2015 | Shelton, IV ........... G16H 40/63 227/181.1 |
| 2015/0173789 | A1* | 6/2015 | Baxter, III ....... A61B 17/07207 606/130 |
| 2015/0272569 | A1* | 10/2015 | Leimbach ................ H02J 5/00 227/175.1 |
| 2015/0272570 | A1* | 10/2015 | Lytle, IV ............. A61B 17/068 227/180.1 |
| 2015/0272575 | A1* | 10/2015 | Leimbach ........... A61B 17/072 227/175.3 |
| 2015/0272578 | A1* | 10/2015 | Leimbach ................ B25F 5/00 227/180.1 |
| 2015/0272579 | A1* | 10/2015 | Leimbach ................ H02J 5/00 227/178.1 |
| 2015/0272580 | A1* | 10/2015 | Leimbach ........... H01M 10/425 227/175.1 |
| 2015/0272583 | A1* | 10/2015 | Leimbach ............... A61L 2/087 227/180.1 |
| 2015/0280384 | A1* | 10/2015 | Leimbach .............. A61B 90/98 227/175.1 |
| 2016/0066909 | A1* | 3/2016 | Baber ................ A61B 17/0644 227/176.1 |
| 2016/0066910 | A1* | 3/2016 | Baber .................... A61B 90/98 227/180.1 |
| 2016/0066912 | A1* | 3/2016 | Baber ...................... G06F 1/305 307/64 |
| 2016/0066913 | A1* | 3/2016 | Swayze .................... H02H 3/06 227/176.1 |
| 2016/0066915 | A1* | 3/2016 | Baber ...................... G06F 1/28 227/178.1 |
| 2016/0066916 | A1* | 3/2016 | Overmyer ............ A61B 5/6847 227/176.1 |
| 2016/0100839 | A1* | 4/2016 | Marczyk .......... A61B 17/07207 227/175.3 |
| 2017/0086823 | A1 | 3/2017 | Leimbach et al. |
| 2017/0168187 | A1* | 6/2017 | Calderoni .............. A61B 90/98 |

OTHER PUBLICATIONS

U.S. Appl. No. 15/634,418, filed Jun. 27, 2017.
U.S. Appl. No. 15/634,436, filed Jun. 27, 2017.
U.S. Appl. No. 15/634,452, filed Jun. 27, 2017.
U.S. Appl. No. 15/634,475, filed Jun. 27, 2017.
U.S. Appl. No. 15/634,524, filed Jun. 27, 2017.
U.S. Appl. No. 15/634,556, filed Jun. 27, 2017.
U.S. Appl. No. 15/634,589, filed Jun. 27, 2017.
U.S. Appl. No. 15/634,620, filed Jun. 27, 2017.
European Search Report and Written Opinion dated Nov. 9, 2018 for Application No. EP 18180123.4, 9 pgs.
International Search Report and Written Opinion dated Sep. 3, 2018 for Application No. PCT/IB2018/053586, 11 pgs.

* cited by examiner

MODULAR POWERED ELECTRICAL CONNECTION FOR SURGICAL INSTRUMENT WITH FEATURES TO PREVENT ELECTRICAL DISCHARGE

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in various ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,000,818, entitled "Surgical Stapling Instrument Having Separate Distinct Closing and Firing Systems," issued Feb. 21, 2006; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. Patent Application Publication No. 2014/0243801, entitled "Surgical Instrument End Effector Articulation Drive with Pinion and Opposing Racks," published on Aug. 28, 2014, issued as U.S. Pat. No. 9,186,142 on Nov. 17, 2015; U.S. Patent Application Publication No. 2014/0239041, entitled "Lockout Feature for Movable Cutting Member of Surgical Instrument," Published Aug. 28, 2014, issued as U.S. Pat. No. 9,717,497 on Aug. 1, 2017; U.S. Patent Application Publication No. 2014/0239038, entitled "Surgical Instrument with Multi-Diameter Shaft," published Aug. 28, 2014, issued as U.S. Pat. No. 9,795,379 on Oct. 24, 2017; and U.S. Patent Application Publication No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Applications is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
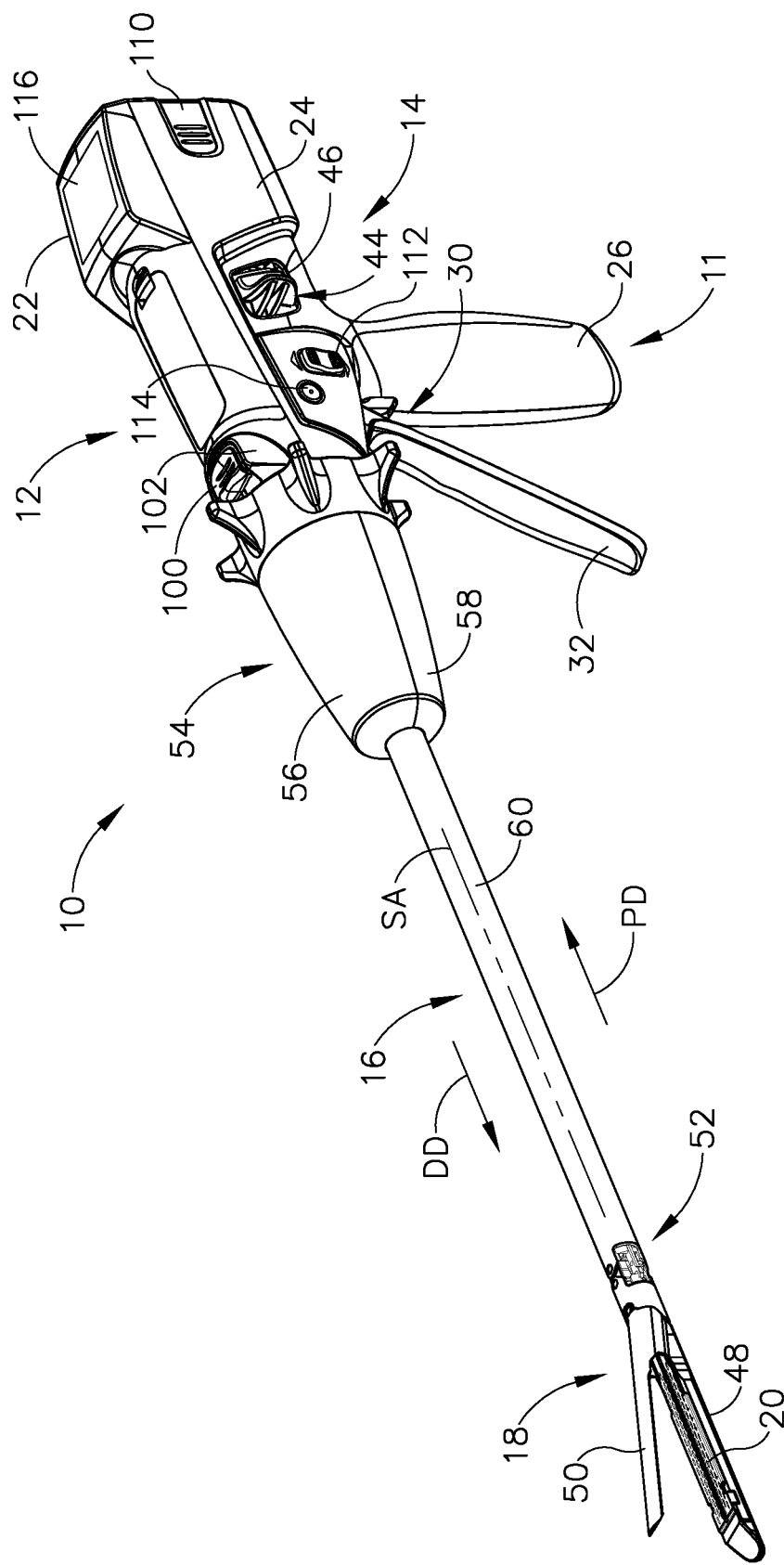
FIG. 1 depicts a perspective view of an exemplary surgical instrument including an interchangeable shaft assembly and a handle assembly.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator. Although the surgical instruments described herein comprise motorized implements for cutting and stapling, it will be appreciated that the configurations described herein may be used with any suitable type of electrical surgical instrument such as cutters, claspers, staplers, RF cutter/coagulators, ultrasonic cutter/coagulators, and laser cutter/coagulators, for example.

I. Overview of Exemplary Surgical Instrument

FIG. 1 depicts a motor-driven surgical cutting and fastening instrument (10) that includes a handle assembly (11) and a removable shaft assembly (16). In some versions, handle assembly (11) and shaft assembly (16) are each provided a single-use, disposable components. In some other versions, handle assembly (11) and shaft assembly (16) are each provided as reusable components. As another merely illustrative example, shaft assembly (16) may be provided as a single-use, disposable component while handle assembly is provided as a reusable component. Various suitable ways in which reusable versions of handle assembly (11) and shaft assembly (16) may be suitable reprocessed for reuse will be apparent to those of ordinary skill in the art in view of the teachings herein.

Handle assembly (11) of the present example includes a housing (12), a closure trigger (32), and a firing trigger (33). At least a portion of housing (12) forms a handle (14) that is configured to be grasped, manipulated and actuated by the clinician. Housing (12) is configured for operative attachment to shaft assembly (16), which has a surgical end effector (18) operatively engaged thereto. As described below, end effector (18) is configured to perform one or more surgical tasks or procedures. In particular, end effector (18) of the example shown in FIG. 1 is operable to perform a surgical cutting and stapling procedure, in a manner similar to an end effector of a conventional endocutter, though it should be understood that this is just one merely illustrative example.

Figure 2:
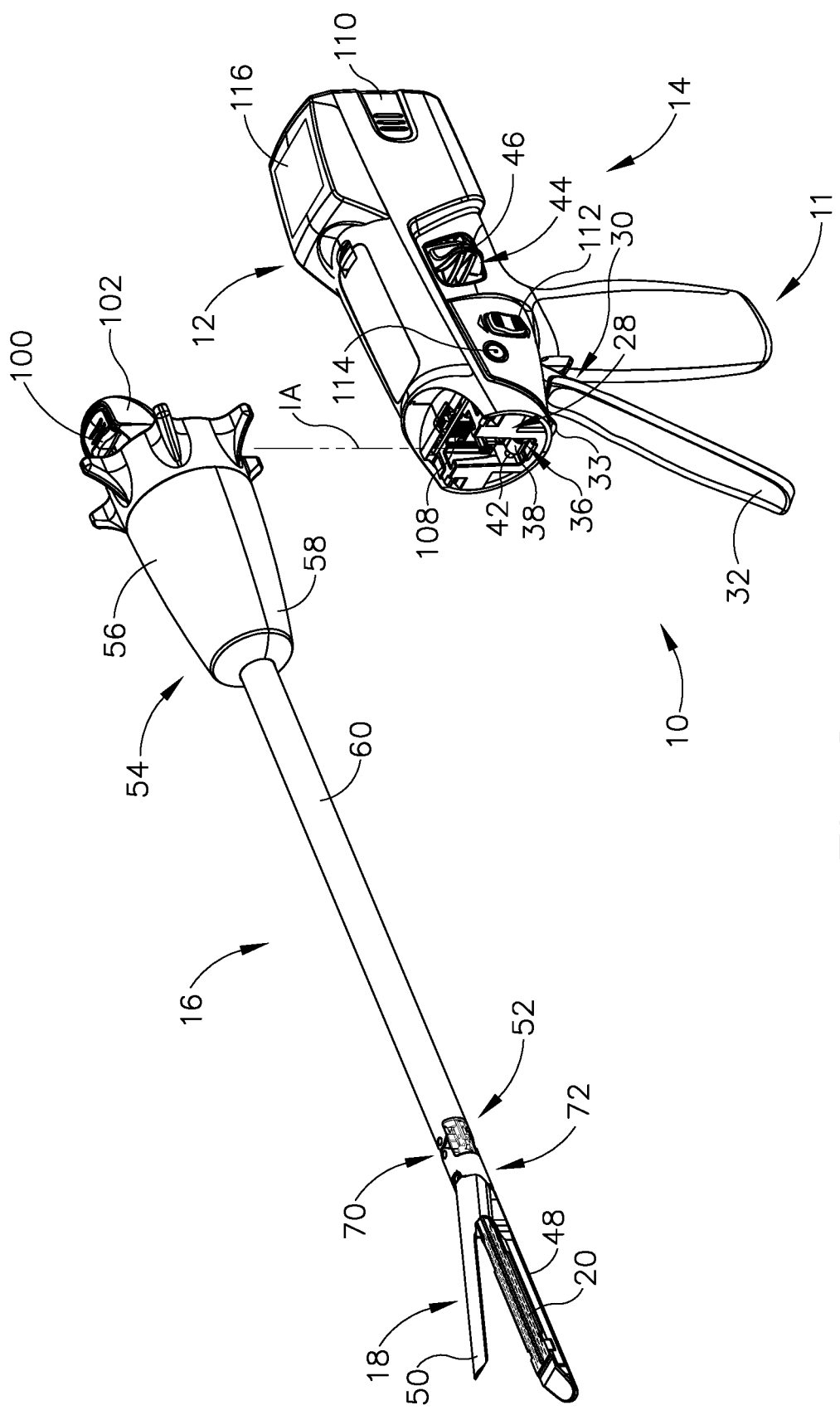
FIG. 2 depicts a perspective view of the instrument of FIG. 1, showing the shaft assembly disassembled from the handle assembly of the instrument.
Figure 3:
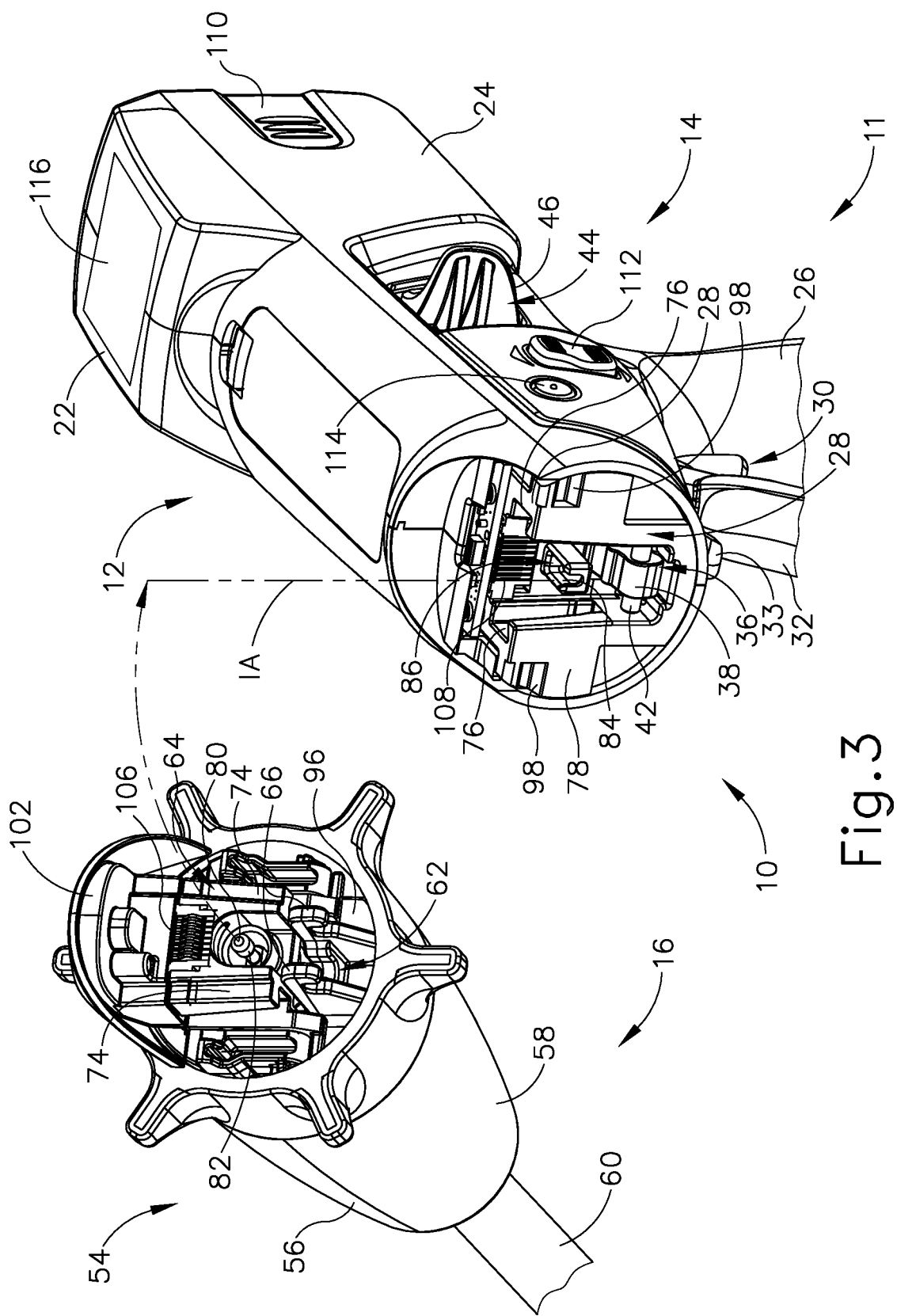
FIG. 3 depicts a partial perspective view of the instrument of FIG. 1, showing the shaft assembly disassembled from the handle assembly of the instrument.

FIG. 1 illustrates surgical instrument (10) with interchangeable shaft assembly (16) operatively engaged to handle assembly (11). FIGS. 2-3 illustrate attachment of interchangeable shaft assembly (16) to housing (12) of handle (14). Handle (14) includes a pair of interconnectable handle housing segments (22, 24) that may be interconnected by screws, snap features, adhesive, etc. In the illustrated arrangement, handle housing segments (22, 24) cooperate to form a pistol grip portion (26) that can be grasped and manipulated by the clinician. As will be discussed in further detail below, handle (14) operatively supports a plurality of drive systems therein that are configured to generate and apply various control motions to corresponding portions of interchangeable shaft assembly (16) that is operatively attached thereto. As will also be discussed in further detail below, triggers (32, 33) are pivotable toward pistol grip portion (26) to activate at least some of the drive systems in handle (14).

Figure 5:
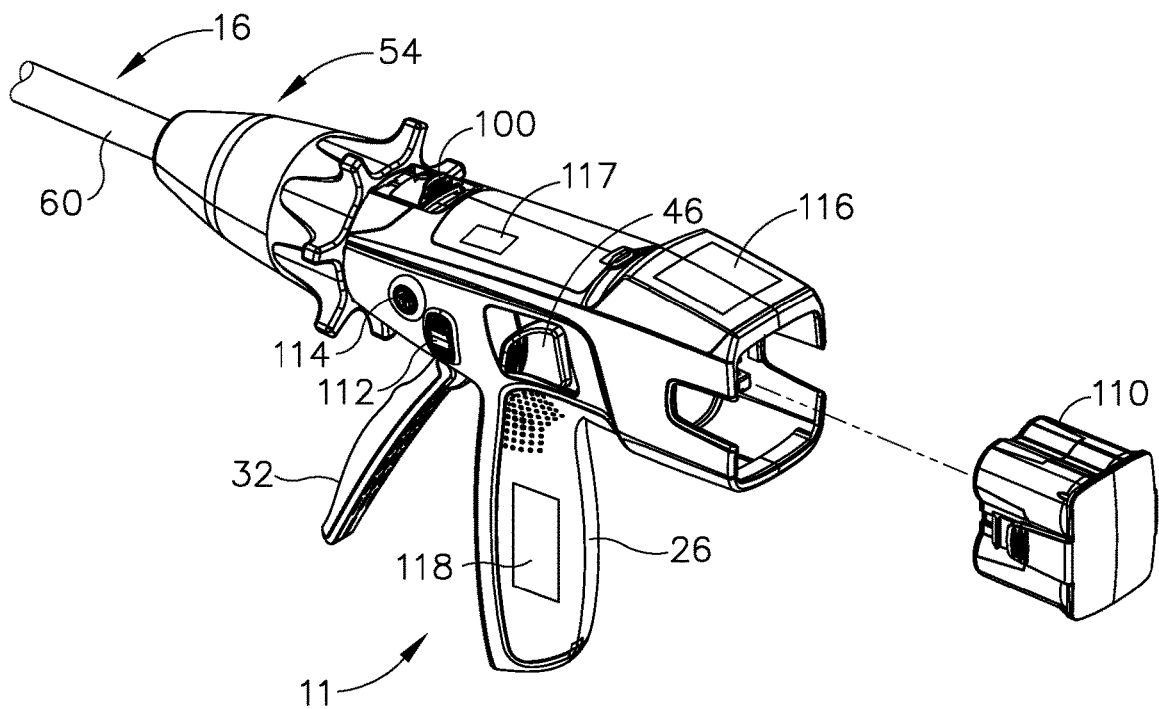
FIG. 5 depicts a perspective view of a proximal portion of the instrument of FIG. 1, with a battery removed from the handle assembly.

At least some of the drive systems in handle assembly (11) are ultimately driven by a motor (118), which is shown schematically in FIG. 5. In the present example, motor (118) is located in pistol grip portion (26), though it should be understood that motor (118) may be located at any other suitable position. Motor (118) receives power from a battery pack (110), which is secured to handle (14). In the present example, and as shown in FIG. 5, battery pack (110) is removable from handle (14). In some other versions, battery pack (110) is not removable from handle (14). In some such versions, battery pack (110) (or a variation thereof) is fully contained within handle housing segments (22, 24). Various suitable forms that motor (118) and battery pack (110) may take will be apparent to those of ordinary skill in the art in view of the teachings herein.

As also shown schematically in FIG. 5, a control circuit (117) is contained within handle (14). By way of example only, control circuit (117) may comprise a microcontroller and/or various other components as will be apparent to those of ordinary skill in the art in view of the teachings herein. Control circuit (117) is configured to store and execute control algorithms to drive motor (118). Control circuit (117) is also configured to drive a graphical user interface (116), which is located at the proximal end of handle assembly (11). In some versions, control circuit (117) is configured to receive and process one or more signals from shaft assembly (16). By way of example only, control circuit (117) may be configured and operable in accordance with at least some of the teachings of U.S. Pub. No. 2015/0272575, entitled "Surgical Instrument Comprising a Sensor System," published Oct. 1, 2015, issued as U.S. Pat. No. 9,913,642 on Mar. 13, 2018, the disclosure of which is incorporated by reference herein. Other suitable ways in which control circuit (117) may be configured and operable will be apparent to those of ordinary skill in the art in view of the teachings herein.

As best seen in FIG. 3, a frame (28) of handle (14) operatively supports a plurality of drive systems. In this particular example, frame (28) operatively supports a "first" or closure drive system, generally designated as (30), which may be employed to apply closing and opening motions to interchangeable shaft assembly (16) that is operatively attached or coupled thereto. Also in this particular example, closure drive system (30) includes an actuator in the form of a closure trigger (32) that is pivotally supported by frame (28). More specifically, closure trigger (32) is pivotally coupled to housing (14) by a pin (not shown). Such arrangement enables closure trigger (32) to be manipulated by a clinician such that when the clinician grasps pistol grip portion (26) of handle (14), closure trigger (32) may be easily pivoted from a starting or "unactuated" position (FIG. 4A) toward pistol grip portion (26) to an "actuated" position; and more particularly to a fully compressed or fully actuated position (FIG. 4B). Closure trigger (32) may be biased into the unactuated position by spring or other biasing arrangement (not shown).

In the present example, closure drive system (30) further includes a closure linkage assembly (36) pivotally coupled to closure trigger (32). A portion of closure linkage assembly (36) is shown in FIG. 3. Closure linkage assembly (36) may include a first closure link (not shown) and a second closure link (38) that are pivotally coupled to closure trigger (32) by a pin (not shown). Second closure link (38) may also be referred to herein as an "attachment member" and includes a transverse attachment pin (42). As shown in FIG. 3, attachment pin (42) is exposed when shaft assembly (16) is detached from handle assembly (11). Attachment pin (42) may thus couple with a complementary feature of a shaft assembly (16) when shaft assembly (16) is coupled with handle assembly (11), as described in greater detail below.

Still referring to FIGS. 1-3, first closure link (not shown) is configured to cooperate with a closure release assembly (44) that is pivotally coupled to frame (28). In at least one example, closure release assembly (44) has a release button assembly (46) with a distally protruding locking pawl (not shown) formed thereon. Release button assembly (46) may be pivoted in a counterclockwise direction by a release spring (not shown). As the clinician depresses closure trigger (32) from its unactuated position toward pistol grip portion (26) of handle (14), first closure link (not shown) pivots upwardly to a point where a locking pawl (not shown) drops into retaining engagement with first closure link (not shown), thereby preventing closure trigger (32) from returning to the unactuated position. Thus, closure release assembly (44) serves to lock closure trigger (32) in the fully actuated position.

When the clinician desires to unlock closure trigger (32) from the actuated position to return to the unactuated position, the clinician simply pivots closure release button assembly (46) by urging release button assembly (46) distally, such that locking pawl (not shown) is moved out of engagement with the first closure link (not shown). When the locking pawl (not shown) has been moved out of engagement with first closure link (not shown), closure trigger (32) may return back to the unactuated position in response to a resilient bias urging closure trigger (32) back to the unactuated position. Other closure trigger locking and release arrangements may also be employed.

Interchangeable shaft assembly (16) further includes an articulation joint (52) and an articulation lock (not shown) that can be configured to releasably hold end effector (18) in a desired position relative to a longitudinal axis of shaft assembly (16). In the present example, articulation joint (52) is configured to allow end effector (18) to be laterally deflected away from the longitudinal axis of shaft assembly (16), as is known in the art. By way of example only, end effector (18), articulation joint (52), and the articulation lock (not shown) may be configured and operable in accordance with at least some of the teachings of U.S. Pub. No. 2014/0263541, entitled "Articulatable Surgical Instrument Comprising an Articulation Lock," published Sep. 18, 2014, now abandoned.

In the present example, articulation at articulation joint (52) is motorized via motor (118), based on control input from the operator via an articulation control rocker (112) on handle assembly (11). By way of example only, when the operator presses on the upper portion of articulation control rocker (112), end effector (18) may laterally pivot to the right (viewing instrument (10) from above) at articulation joint (52); and when the operator presses on the lower portion of articulation control rocker (112), end effector (18) may laterally pivot to the left (viewing instrument (10) from above) at articulation joint (52). In some versions, the other side of handle assembly (11) includes another articulation control rocker (112). In such versions, the articulation control rocker (112) on the other side of handle assembly (11) may be configured to provide pivoting of end effector (18) in directions opposite to those listed above in response to upper actuation of articulation control rocker (112) and lower actuation of articulation control rocker (112). By way of example only, articulation control rocker (112) and the rest of the features that provide motorized articulation of end effector (18) at articulation joint (52) may be configured and operable in accordance with at least some of the teachings of U.S. Pub. No. 2015/0280384, entitled "Surgical Instrument Comprising a Rotatable Shaft," published Oct. 1, 2015, issued as U.S. Pat. No. 10,201,364 on Feb. 12, 2019, the disclosure of which is incorporated by reference herein. Other suitable ways in which articulation control rocker (112) and the rest of the features that provide motorized articulation of end effector (18) at articulation joint (52) may be configured and operable will be apparent to those of ordinary skill in the art in view of the teachings herein.

End effector (18) of the present example comprises a lower jaw in the form of an elongated channel (48) that is configured to operatively a support staple cartridge (20) therein. End effector (18) of the present example further includes an upper jaw in the form of an anvil (50) that is pivotally supported relative to elongated channel (48). Interchangeable shaft assembly (16) further includes a proximal housing or nozzle (54) comprised of nozzle portions (56, 58); and a closure tube (60) that can be utilized to close and/or open anvil (50) of end effector (18). Shaft assembly (16) also includes a closure shuttle (62) that is slidably supported within a chassis (64) of shaft assembly (16) such that closure shuttle (62) may be axially moved relative to chassis (64). Closure shuttle (62) includes a pair of proximally-protruding hooks (66) that are configured for attachment to attachment pin (42) that is attached to second closure link (38). A proximal end (not shown) of closure tube (60) is coupled to closure shuttle (62) for relative rotation thereto, though the coupling of closure tube (60) with closure shuttle (62) provides that closure tube (60) and closure shuttle (62) will translate longitudinally with each other. A closure spring (not shown) is journaled on closure tube (60) and serves to bias closure tube (60) in the proximal direction (PD), which can serve to pivot closure trigger (32) into the unactuated position when shaft assembly (16) is operatively engaged to handle (14).

In the present example, articulation joint (52) includes a double pivot closure sleeve assembly (70). Double pivot closure sleeve assembly (70) includes an end effector closure sleeve assembly (72) for engaging an opening tab on anvil (50) in the various manners described in U.S. Pub. No. 2014/0263541, now abandoned, the disclosure of which is incorporated by reference herein. It should be understood that double pivot closure sleeve assembly (70) is coupled with closure tube (60) such that double pivot closure sleeve assembly (70) translates with closure tube (60) in response to pivotal movement of closure trigger (32), even when articulation joint (52) is in an articulated state (i.e., when end effector (18) is pivotally deflected laterally away from the longitudinal axis of shaft assembly (16) at articulation joint (52)). Moreover, the engagement of end effector closure sleeve assembly (72) with anvil (50) provides pivotal movement of anvil (50) toward staple cartridge (20) in response to distal translation of double pivot closure sleeve assembly (70) and closure tube (60); and pivotal movement of anvil (50) away from staple cartridge (20) in response to proximal translation of double pivot closure sleeve assembly (70) and closure tube (60). While shaft assembly (16) of the present example includes articulation joint (52), other interchangeable shaft assemblies may lack articulation capabilities.

As shown in FIG. 3, chassis (64) includes a pair of tapered attachment portions (74) formed thereon that are adapted to be received within corresponding dovetail slots (76) formed within a distal attachment flange portion (78) of frame (28). Each dovetail slot (76) may be tapered or generally V-shaped to seatingly receive attachment portions (74) therein. A shaft attachment lug (80) is formed on the proximal end of an intermediate firing shaft (82). Thus, when interchangeable shaft assembly (16) is coupled to handle (14), shaft attachment lug (80) is received in a firing shaft attachment cradle (84) formed in a distal end of a longitudinal drive member (86). When shaft attachment lug (80) is received in firing shaft attachment cradle (84), intermediate firing shaft (82) will translate longitudinally with longitudinal drive member (86). When intermediate firing shaft (82) translates distally, intermediate firing shaft (82) actuates end effector (18) to drive staples into tissue and cut the tissue, as is known in the art. By way of example only, this actuation of end effector (18) may be carried out in accordance with at least some of the teachings of U.S. Pub. No. 2015/0280384, issued as U.S. Pat. No. 10,201,364 on Feb. 12, 2019, the disclosure of which is incorporated by reference herein; and/or in accordance with the teachings of various other references cited herein.

Figure 4A:
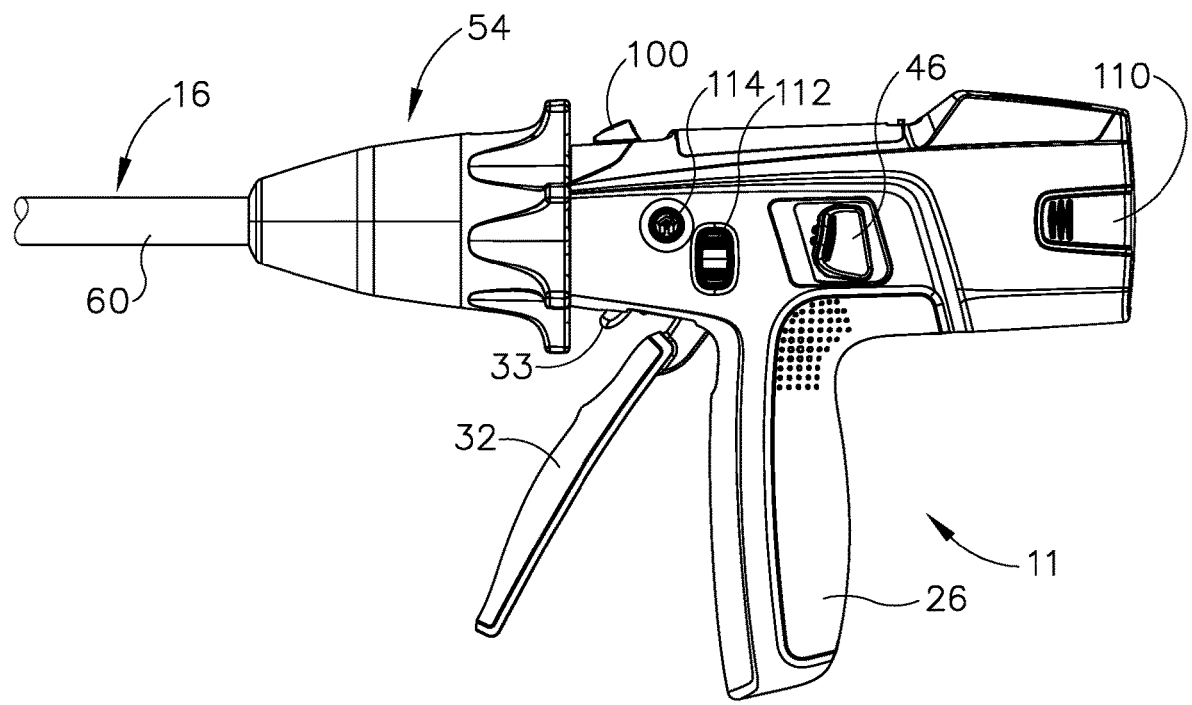
FIG. 4A depicts a side elevational view of a proximal portion of the instrument of FIG. 1, with a closure trigger in a first pivotal position and a firing trigger in a first pivotal position.
Figure 4B:
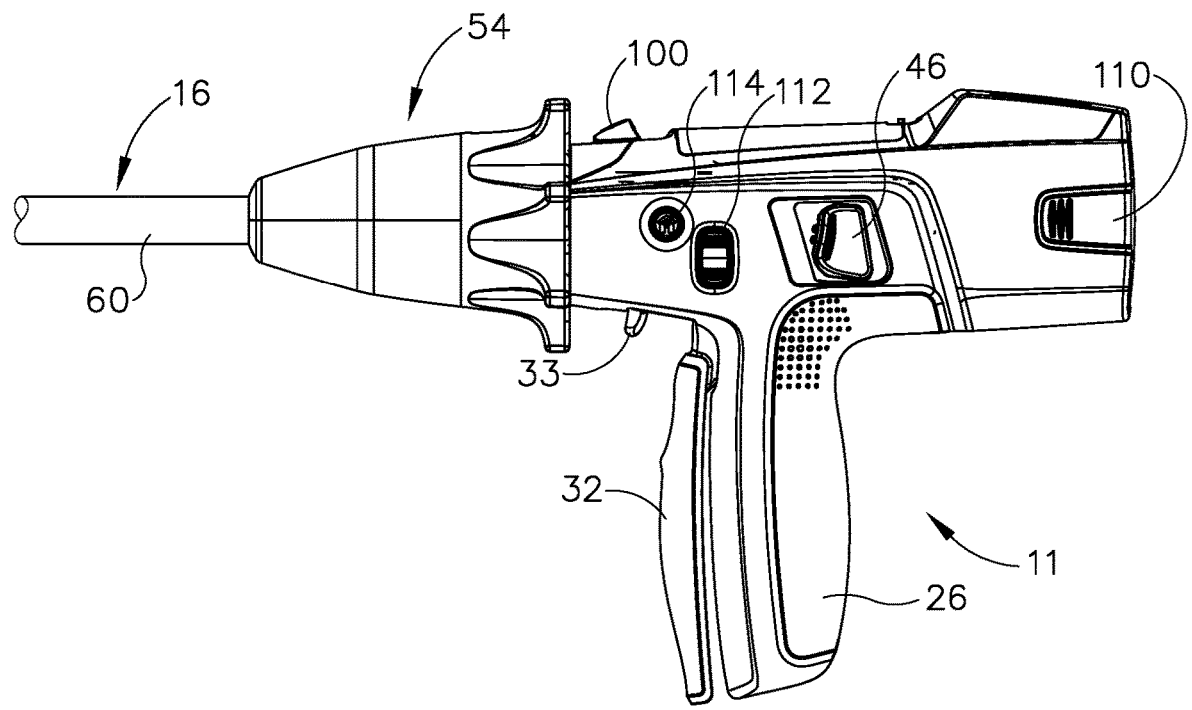
FIG. 4B depicts a side elevational view of a proximal portion of the instrument of FIG. 1, with the closure trigger in a second pivotal position and the firing trigger in a second pivotal position.
Figure 4C:
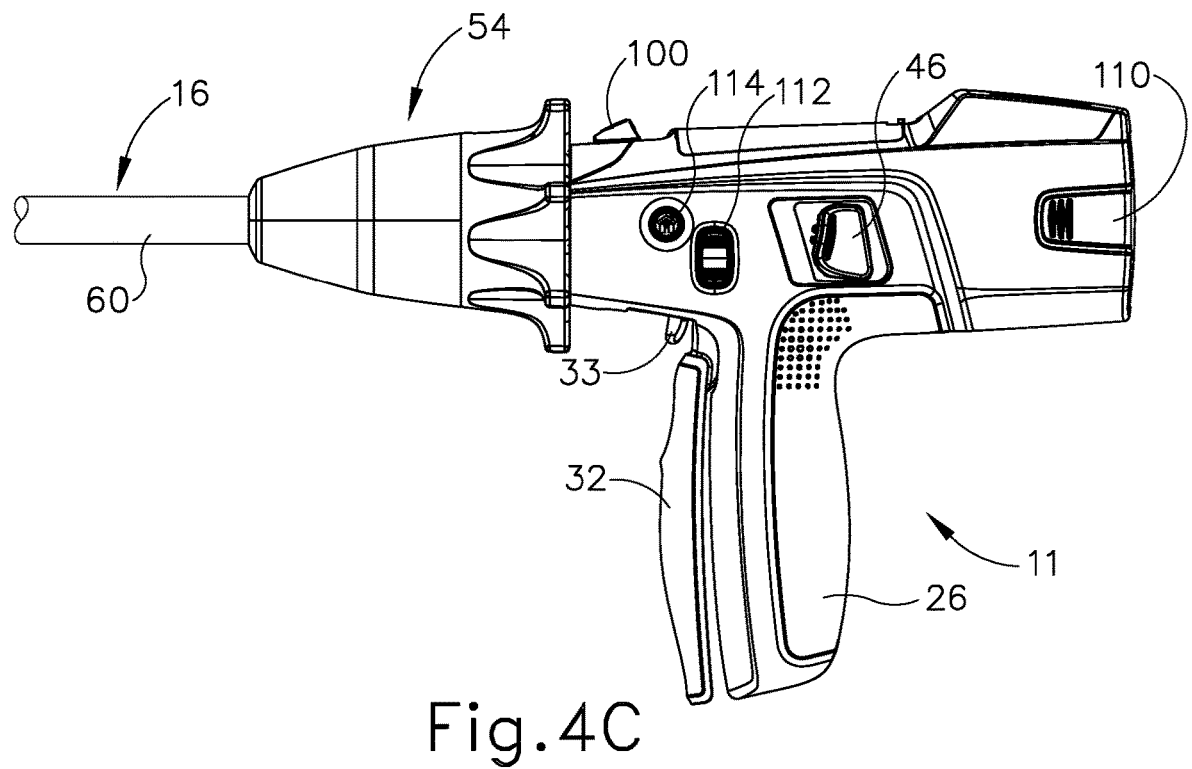
FIG. 4C depicts a side elevational view of a proximal portion of the instrument of FIG. 1, with the closure trigger in the second pivotal position and the firing trigger in a third pivotal position.

FIGS. 4A-4C show the different states of handle assembly (11) during the different states of actuation of end effector (18). In FIG. 4A, handle assembly (11) is in a state where closure trigger (32) is in a non-actuated pivotal position and firing trigger (33) is in a non-actuated pivotal position. At this stage, end effector (18) is in an opened state where anvil (50) is pivoted away from staple cartridge (20).

In FIG. 4B, handle assembly (11) is in a state where closure trigger (32) is in an actuated pivotal position. As noted above, closure trigger (32) will be locked in this position until the operator actuates release button assembly (46). At this stage, end effector is in a closed but unfired state where anvil (50) is pivoted toward staple cartridge (20), such that tissue is being compressed between anvil (50) and cartridge (20). However, firing shaft (82) has not yet been driven distally to actuate staples from staple cartridge (20), and the knife at the distal end of firing shaft (82) has not yet severed the tissue between anvil (20) and staple cartridge (20). It should be noted that firing trigger (33) is in a partially-actuated pivotal position in FIG. 4B, due to the travel of closure trigger (32) from the non-actuated pivotal position to the actuated pivotal position. However, this movement of firing trigger (33) is only provided in order to improve access to firing trigger (33) for the operator. In other words, this movement of firing trigger (33) from the position shown in FIG. 4A to the position shown in FIG. 4B does not yet activate a firing sequence.

In FIG. 4C, handle assembly is in a state where closure trigger (32) remains in the actuated pivotal position, and firing trigger (33) has been pivoted to an actuated pivotal position. This actuation of firing trigger (33) activates motor (118) to drive longitudinal drive member (86) longitudinally, which in turn drives firing shaft (82) longitudinally. The longitudinal movement of firing shaft (82) results in actuation of staples from staple cartridge (20) into the tissue compressed between anvil (50) and staple cartridge (20); and further results in the severing of the tissue compressed between anvil (50) and staple cartridge (20). In some versions, an additional safety trigger is provided. For instance, the additional safety trigger may prevent actuation of firing trigger (33) until the safety trigger is actuated. In other words, after reaching the state shown in FIG. 4B, when the operator is ready to actuate firing trigger (33), the operator must first actuate the safety trigger and then actuate firing trigger (33). It should be understood that the presence of a safety trigger may prevent inadvertent actuation of firing trigger (33).

It should also be understood that, in the present example, the actuation of anvil (50) toward staple cartridge (20) is provided through purely mechanical couplings between closure trigger (32) and anvil (50), such that motor (118) is not used to actuate anvil (50). It should also be understood that, in the present example, the actuation of firing shaft (82) (and, hence, the actuation of staple cartridge (20)) is provided through activation of motor (118). In addition, the actuation of articulation joint (52) is provided through activation of motor (118) in the present example. This motorized actuation of articulation joint (52) is provided via longitudinal translation of drive member (86). A clutch assembly (not shown) within shaft assembly (16) is operable to selectively couple longitudinal translation of drive member (86) with features to either drive articulation joint (52) or actuate staple cartridge (20). Such selective coupling via the clutch assembly is based on the pivotal position of closure trigger (32). In particular, when closure trigger (32) is in the non-actuated position shown in FIG. 4A, activation of motor (118) (in response to activation of articulation control rocker (112)) will drive articulation joint (52). When closure trigger (32) is in the actuated position shown in FIG. 4B, activation of motor (118) (in response to actuation of firing trigger (33)) will actuate staple cartridge (20). By way of example only, the clutch assembly may be configured and operable in accordance with at least some of the teachings of U.S. Pub. No. 2015/0280384, issued as U.S. Pat. No. 10,201,364 on Feb. 12, 2019, the disclosure of which is incorporated by reference herein.

In the present example, handle assembly (11) also includes a "home" button (114). By way of example only, when anvil (50) is in a closed position, "home" button (114) may be operable to activate motor (118) to retract drive member (86) proximally to a proximal-most, "home" position. In addition, or in the alternative, when anvil (50) is in an open position, "home" button (114) may be operable to activate motor (118) to drive articulation joint (52) to achieve a non-articulated state, such that end effector (18) is coaxially aligned with shaft assembly (16). In addition, or in the alternative, "home" button (114) may activate graphical user interface (116) to return to a "home" screen. Other suitable operations that may be provided in response to activation of "home" button (114) will be apparent to those of ordinary skill in the art in view of the teachings herein.

Shaft assembly (16) of the present example further includes a latch system for removably coupling shaft assembly (16) to handle assembly (11) and, more specifically, to frame (28). By way of example only, this latch system may include a lock yoke or other kind of lock member that is movably coupled to chassis (64). As shown in FIG. 3, such a lock yoke may include two proximally protruding lock lugs (96) that are configured for releasable engagement with corresponding lock detents or grooves (98) in frame (28). In some versions, the lock yoke is biased in the proximal direction by a resilient member (e.g., a spring, etc.). Actuation of the lock yoke may be accomplished by a latch button (100) that is slidably mounted on a latch actuator assembly (102) that is mounted to chassis (64). Latch button (100) may be biased in a proximal direction relative to the lock yoke. The lock yoke may be moved to an unlocked position by urging latch button (100) the in distal direction, which also causes the lock yoke to pivot out of retaining engagement with frame (28). When the lock yoke is in "retaining engagement" with frame (28), lock lugs (96) are retainingly seated within the corresponding lock detents or grooves (98). By way of further example only, shaft assembly (16) may be removably coupled with handle assembly (11) in accordance with at least some of the teachings of U.S. Pub. No. 2017/0086823, entitled "Surgical Stapling Instrument with Shaft Release, Powered Firing, and Powered Articulation," published Mar. 30, 2017, issued as U.S. Pat. No. 10,182,813 on Jan. 22, 2019, the disclosure of which is incorporated by reference herein; in accordance with at least some of the teachings of U.S. Pub. No. 2015/0280384, issued as U.S. Pat. No. 10,201,364 on Feb. 12, 2019, the disclosure of which is incorporated by reference herein; and/or in any other suitable fashion.

To commence the coupling process between shaft assembly (16) and handle assembly (11), the clinician may position chassis (64) of interchangeable shaft assembly (16) above or adjacent to frame (28) such that tapered attachment portions (74) formed on chassis (64) are aligned with dovetail slots (76) in frame (28). The clinician may then move shaft assembly (16) along an installation axis (IA) that is perpendicular to the longitudinal axis of shaft assembly (16) to seat attachment portions (74) in "operative engagement" with the corresponding dovetail receiving slots (76). In doing so, shaft attachment lug (80) on intermediate firing shaft (82) will also be seated in cradle (84) in the longitudinally movable drive member (86) and the portions of pin (42) on second closure link (38) will be seated in the corresponding hooks (66) in closure shuttle (62). As used herein, the term "operative engagement" in the context of two components means that the two components are sufficiently engaged with each other so that upon application of an actuation motion thereto, the components may carry out their intended action, function, and/or procedure.

As discussed above, at least five systems of interchangeable shaft assembly (16) may be operatively engaged with at least five corresponding systems of handle (14). A first system comprises a frame system that couples and/or aligns the frame or spine of shaft assembly (16) with frame (28) of the handle (14). A second system is the latch system that releasably locks the shaft assembly (16) to the handle (14).

A third system is closure drive system (30) that may operatively connect closure trigger (32) of handle (14) and closure tube (60) and anvil (50) of shaft assembly (16). As outlined above, closure shuttle (62) of shaft assembly (16) engages with pin (42) on second closure link (38). Through closure drive system (30), anvil (50) pivots toward and away from staple cartridge (20) based on pivotal movement of closure trigger (32) toward and away from pistol grip (26).

A fourth system is an articulation and firing drive system operatively connecting firing trigger (33) of handle (14) with intermediate firing shaft (82) of the shaft assembly (16). As outlined above, the shaft attachment lug (80) operatively connects with the cradle (84) of the longitudinal drive member (86). This fourth system provides motorized actuation of either articulation joint (52) or staple cartridge (20), depending on the pivotal position of closure trigger (32). When closure trigger (32) is in a non-actuated pivotal position, the fourth system operatively connects articulation control rocker (112) with articulation joint (52), thereby providing motorized pivotal deflection of end effector (18) toward and away from the longitudinal axis of shaft assembly (11) at articulation joint (52). When closure trigger (32) is in an actuated pivotal position, the fourth system operatively connects firing trigger (33) with staple cartridge (20), resulting in stapling and cutting of tissue captured between anvil (50) and staple cartridge (20) in response to actuation of firing trigger (33).

A fifth system is an electrical system that can signal to control circuit (117) in handle (14) that the shaft assembly (16) has been operatively engaged with the handle (14), to conduct power and/or communicate signals between the shaft assembly (16) and the handle (14). In the present example, and as shown in FIG. 3, shaft assembly (16) includes an electrical connector (106) that is operatively mounted to a shaft circuit board (not shown). Electrical connector (106) is configured for mating engagement with a corresponding electrical connector (108) on a handle control board (not shown). Therefore, electrical connectors (106, 108) may provide communication between control circuit (117) of handle (14) and shaft circuit board (not shown) of shaft assembly (16). Further details regarding the circuitry and control systems may be found in U.S. Pub. No. 2014/0263541, now abandoned, the disclosure of which is incorporated by reference herein and/or U.S. Pub. No. 2015/0272575, issued as U.S. Pat. No. 9,913,642 on Mar. 13, 2018, the disclosure of which is incorporated by reference herein.

Other kinds of systems of interchangeable shaft assembly (16) that may be operatively engaged with at corresponding systems of the handle (14) will be apparent to those of ordinary skill in the art in view of the teachings herein.

As noted above, handle assembly (11) of the present example includes a graphical user interface (116). By way of example only, graphical user interface (116) may be used to display various information about the operational state of battery (110), the operational state of end effector (18), the operational state of articulation joint (52), the operational state of triggers (32, 33), and/or any other kinds of information. Other suitable kinds of information that may be displayed via graphical user interface will be apparent to those of ordinary skill in the art in view of the teachings herein.

Figure 6:
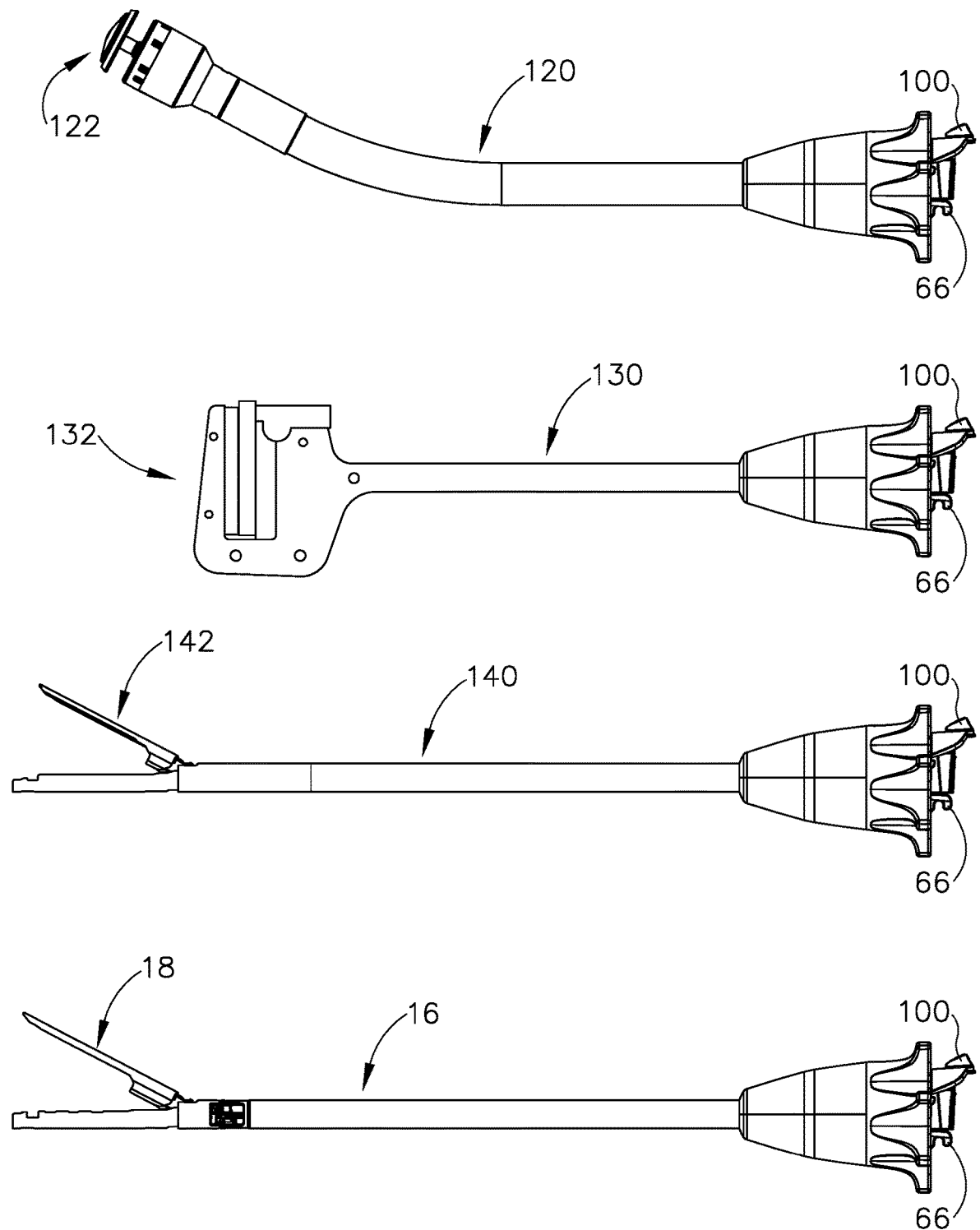
FIG. 6 depicts a side elevational view of an array of alternative shaft assemblies that may be used with the instrument of FIG. 1.

Handle assembly (11) may be configured for use in connection with interchangeable shaft assemblies that include end effectors that are adapted to support different sizes and types of staple cartridges, have different shaft lengths, sizes, and types, etc. By way of example only, FIG. 6 shows various different kinds of shaft assemblies (16, 120, 130, 140) that may be used with handle assembly (11). In particular, FIG. 6 shows a circular stapler shaft assembly (120) with an end effector (122) that is operable to perform a circular stapling operation (e.g., end-to-end anastomosis); a liner stapler shaft assembly (130) with an end effector (132) that is operable to perform a linear stapling operation; and a second endocutter shaft assembly (140) with an end effector (142) that is operable to perform the same kind of stapling and cutting operation as end effector (18). However, in this example, shaft assembly (140) is shorter than shaft assembly (16), shaft assembly (140) has a smaller diameter than shaft assembly (16), and end effector (142) is smaller than end effector (18). It should be understood that these various surgical stapling shaft assemblies (16, 120, 130, 140) are merely illustrative examples.

It should also be understood that control circuit (117) may be configured to detect the kind of shaft assembly (16, 120, 130, 140) coupled with handle assembly (11), and select a control algorithm suited for that particular kind of shaft assembly (16, 120, 130, 140). As another merely illustrative example, each shaft assembly (16, 120, 130, 140) may have a chip or other memory device storing the control algorithm suited for that particular kind of shaft assembly (16, 120, 130, 140); and control circuit (117) may receive and execute that control algorithm after shaft assembly (16, 120, 130, 140) is coupled with handle assembly (11). For example, when operatively engaged, control circuit (117) may establish communication with shaft circuit board (not shown) via electrical connectors (106, 108) such that control circuit (117) may detect which shaft assembly (16, 120, 130, 140) is attached via information from shaft circuit board (not shown).

In addition, handle assembly (11) may also be effectively employed with a variety of other interchangeable shaft assemblies including those assemblies that are configured to apply other motions and kinds of energy such as, for example, radio frequency (RF) energy, ultrasonic energy and/or motion to end effector arrangements adapted for use in connection with various surgical applications and procedures. Furthermore, end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly. Various examples of such cartridges are disclosed in various references that are cited herein.

The various shaft assemblies (16) disclosed herein may employ sensors and various other components that require electrical communication with control circuit (117) in handled assembly (11). The electrical communications may be provided via mating electrical connectors (106, 108). By way of example only, such sensors and other components may be constructed and operable in accordance with at least some of the teachings of U.S. Pub. No. 2015/0272575, issued as U.S. Pat. No. 9,913,642 on Mar. 13, 2018, the disclosure of which is incorporated by reference herein. In addition, or in the alternative, instrument (10) may be constructed and operable in accordance with at least some of the teachings of any of the various other references that are cited herein.

It will be appreciated that the various teachings herein may also be effectively employed in connection with robotically-controlled surgical systems. Thus, the term "housing" or "body" may also encompass a housing, body, or similar portion of a robotic system that houses or otherwise operatively supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operatively control a surgical instrument. By way of example only, the interchangeable shaft assemblies disclosed herein may be employed with any of the various robotic systems, instruments, components and methods disclosed in U.S. Pat. No. 9,072,535, entitled "Surgical Stapling Instruments with Rotatable Staple Deployment Arrangements," issued Jul. 7, 2015, the disclosure of which is incorporated by reference herein.

II. Exemplary Handle Assembly and Shaft Assembly with Two-Step Verification for Selective Energization As noted above, battery pack (110) is operable to power motor (118). Additionally, battery pack (110) is operable to power control circuit (117) such that control circuit (117) may function as described above. Control circuit (117) is in communication with electrical connector (108), such that when handle assembly (11) and shaft assembly (16) are operatively engaged, control circuit (117) is operable to conduct power and/or communicate signals between shaft assembly (16) and handle assembly (11) via electrical connectors (106, 108). Therefore, battery pack (110) may energize electrical connector (108) via control circuit (117). In some instances, it may be desirable to prevent the energization of electrical connector (108) before handle assembly (11) and shaft assembly (16) are properly engaged to prevent accidental electrical discharge at electrical connector (108).

Control circuit (117) may confirm that shaft assembly (16) and handle assembly (11) are properly operatively engaged before control circuit (117) fully energizes electrical connector (108). Additionally, it may be desirable for control circuit (117) to confirm proper operative engagement between shaft assembly (16) and handle assembly (11) with a two-step verification process to further verify proper operative engagement before fully energizing electrical connector (108). Confirming proper operative engagement between shaft assembly (16) and handle assembly (11) before fully energizing electrical connector (108) of handle assembly (11) may help prevent accidental electrical discharge at electrical connector (108).

A. Exemplary Handle Assembly with Proximity Sensors and Shaft Assembly with Proximity Targets FIGS. 7-9B show an exemplary motor driven surgical cutting and fastening instrument (210) including a handle assembly (211) and shaft assembly (216) that may confirm proper operative engagement between each other before fully energizing an electrical connector (292) of handle assembly (211), as mentioned above. Handle assembly (211) is substantially similar to handle assembly (11) described above, with differences described below.

Handle assembly (211) includes a housing (212), a closure trigger (232), a firing trigger (233), a handle (214) including a pair of interconnectable handle housing segments (222, 224) cooperating to form a pistol grip portion (226), a battery pack (215), a frame (228) defining lock detents (298) and including a distal attachment flange portion (278) defining dovetail slots (276), a closure drive system (230), a closure linkage assembly (236), a second closure link (238), a transverse attachment pin (242), a closure release assembly (244) having a release button assembly (246), an articulation control rocker (220), a longitudinal driver member (286) forming a firing shaft attachment cradle (284), a control circuit (217), a graphical user interface (218), a home button (213), and an electrical connector (292); which are substantially similar to housing (12), closure trigger (32), firing trigger (33), handle (14) including a pair of interconnectable handle housing segments (22, 24) cooperating to form pistol grip portion (26), battery pack (110), frame (28) defining lock detents (98) and including distal attachment flange portion (78) defining dovetail slots (76), closure drive system (30), closure linkage assembly (36), second closure link (38), transverse attachment pin (42), closure release assembly (44) having release button assembly (46), articulation control rocker (112), longitudinal driver member (86) forming firing shaft attachment cradle (84), control circuit (117), graphical user interface (116), home button (114), and electrical connector (108) described above, respectively.

Shaft assembly (216) is substantially similar to shaft assembly (16) described above, with differences described below. Shaft assembly (216) includes nozzle (254) including nozzle portions (256, 258), a closure tube (260), a closure shuttle (262) including a pair of proximally-protruding hooks (266), a chassis (264) including a pair of tapered attachment portions (274), an intermediate firing shaft (282) including a shaft attachment lug (280), a pair of proximally protruding lock lugs (296), a latch actuator assembly (288), a shaft circuit board (219), and an electrical connector (290); which are substantially similar to nozzle (54) including nozzle portions (56, 58), closure tube (60), closure shuttle (62) including a pair of proximally-protruding hooks (66), chassis (64) including a pair of tapered attachment portions (74), intermediate firing shaft (82) including shaft attachment lug (80), a pair of proximally protruding lock lugs (96), latch actuator assembly (102), and electrical connector (106), described above, respectively. Shaft assembly (216) includes a shaft circuit board (219) in communication with electrical connector (290).

Shaft assembly (216) may be coupled to handle (214) in a similar fashion to how shaft assembly (16) couples with handle (14) described above. Therefore, when operatively engaged, five systems of interchangeable shaft assembly (216) may be operatively engaged with at least five corresponding systems of handle (214), similar to shaft assembly (16) and handle (14) described above. However, any suitable number of systems of interchangeability between shaft assembly (216) and handle (214) may be incorporated as would be apparent to one having ordinary skill in the art in view of the teachings herein.

Battery pack (215) is operable to selectively power control circuit (217) while control circuit (217) is in communication with electrical connector (292). Additionally, shaft circuit board (219) is in communication with electrical connector (290). When shaft assembly (216) and handle (214) are operatively engaged with each other, control circuit (217) and shaft circuit board (219) are in electrical communication via electrical connectors (292, 290).

Shaft assembly (216) may incorporate any suitable type of end effector as would be apparent to one having ordinary skill in the art in view of the teachings herein. For instance, shaft assembly (216) may incorporate any end effector (18, 122, 132, 142) described above.

Figure 7:
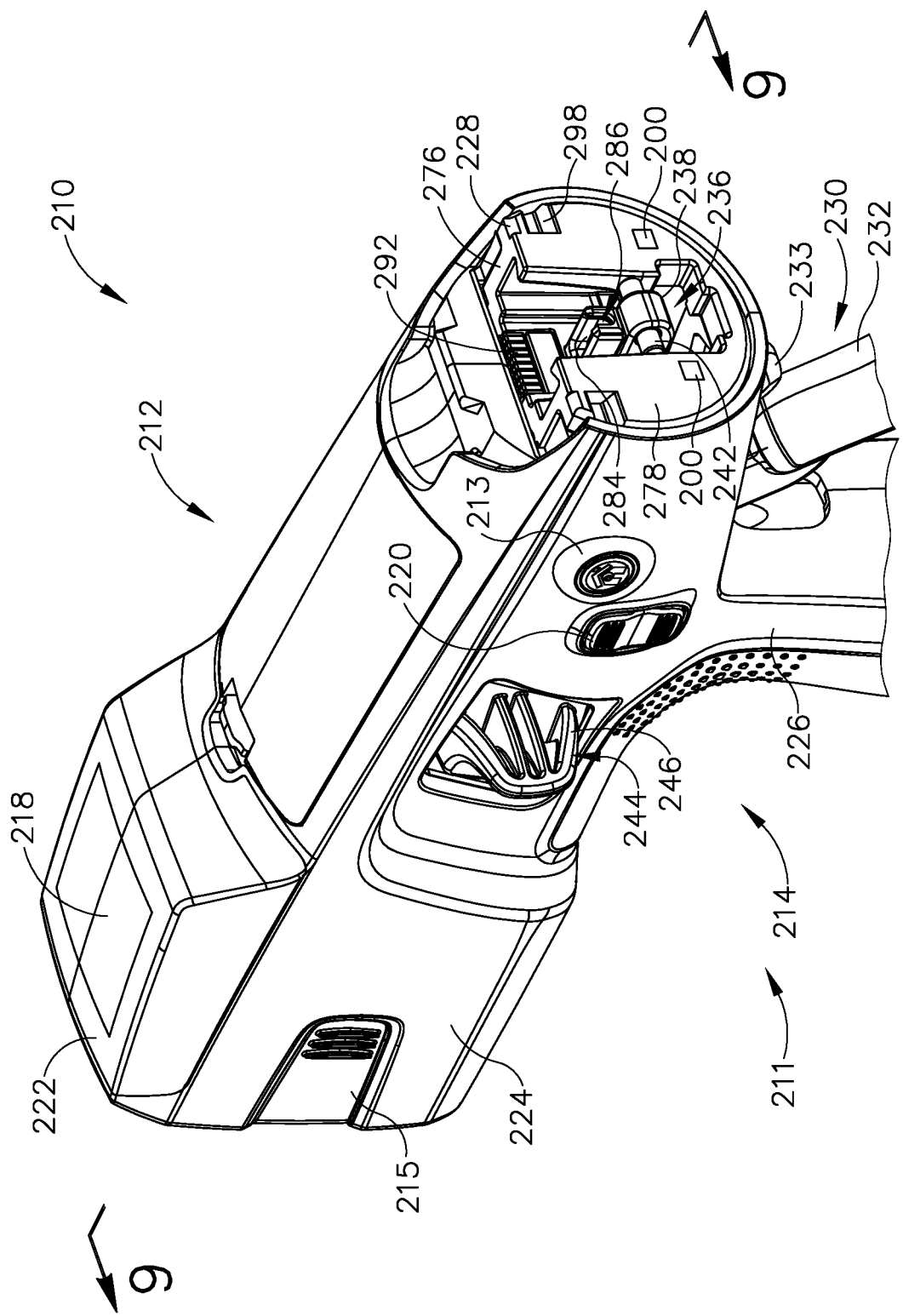
FIG. 7 depicts a perspective view of an exemplary alternative handle assembly that may be incorporated into the instrument of FIG. 1.
Figure 8:
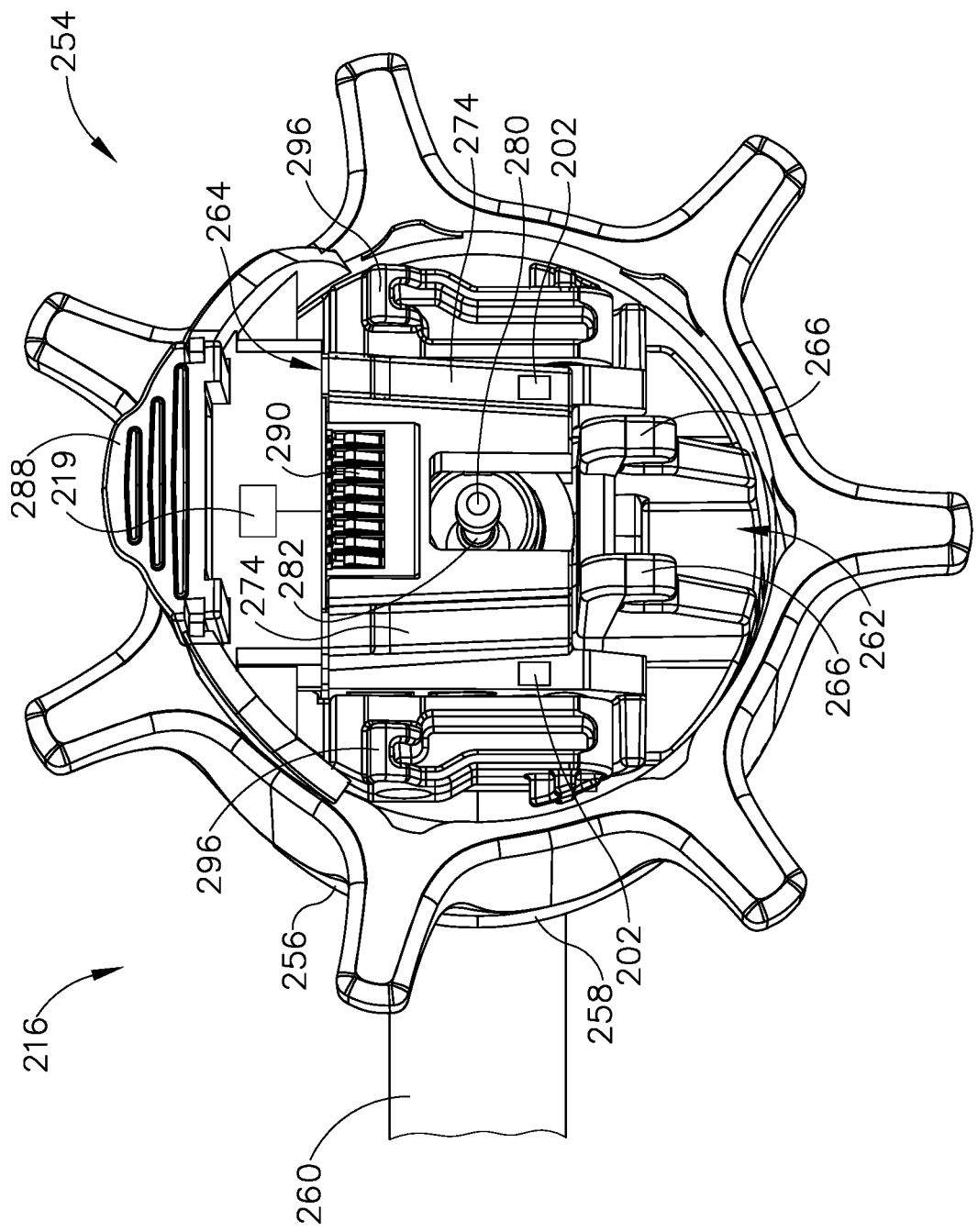
FIG. 8 depicts a perspective view of an exemplary alternative shaft assembly that may be assembled with the handle assembly of FIG. 7 to form a variation of the instrument of FIG. 1.

Additionally, as can be seen in FIG. 7, handle assembly (211) includes a pair of proximity sensors (200) attached to frame (228). Proximity sensors (200) may be located at a distal location on frame (228). As can be seen in FIG. 8, shaft assembly (216) includes a pair of proximity targets (202) attached to chassis (264). Proximity targets (202) may be located at a proximal position on chassis (264). Proximity sensors (200) are configured to detect the presence of proximity targets (202) when proximity sensors (200) are sufficiently close to proximity targets (202). In particular, proximity sensors (200) and proximity targets (202) are located on handle assembly (211) and shaft assembly (216), respectively, such that proximity sensors (200) may detect proximity targets (202) when handle assembly (211) and shaft assembly (216) are operatively engaged. In some instances, proximity targets (202) may abut against proximity sensors (200) when handle assembly (211) and shaft assembly (216) are operatively engaged.

Proximity sensors (200) and proximity targets (202) may include any suitable sensor/target configuration that would be apparent to one having ordinary skill in the art in view of the teachings herein. For instance, proximity sensors (200) may include Hall effect sensors while proximity targets (202) may include magnets, such that Hall effector sensors may detect the presence of magnets when sufficiently close to each other. Alternatively, proximity sensors (200) may include optical sensors housed within handle assembly (211) such that optical sensors are not exposed to ambient light, while proximity targets (202) may include a focused light source configured to direct light toward optical sensors when handle assembly (211) and shaft assembly (216) are operatively engaged. While in the current example, two proximity sensors (200) and two corresponding proximity targets (202)

are used, any suitable number of proximity sensors (200) and corresponding proximity targets (202) may be utilized as would be apparent to one having ordinary skill in the art in view of the teachings herein, such as one proximity sensor (200) and one proximity target (202).

Figure 9A:
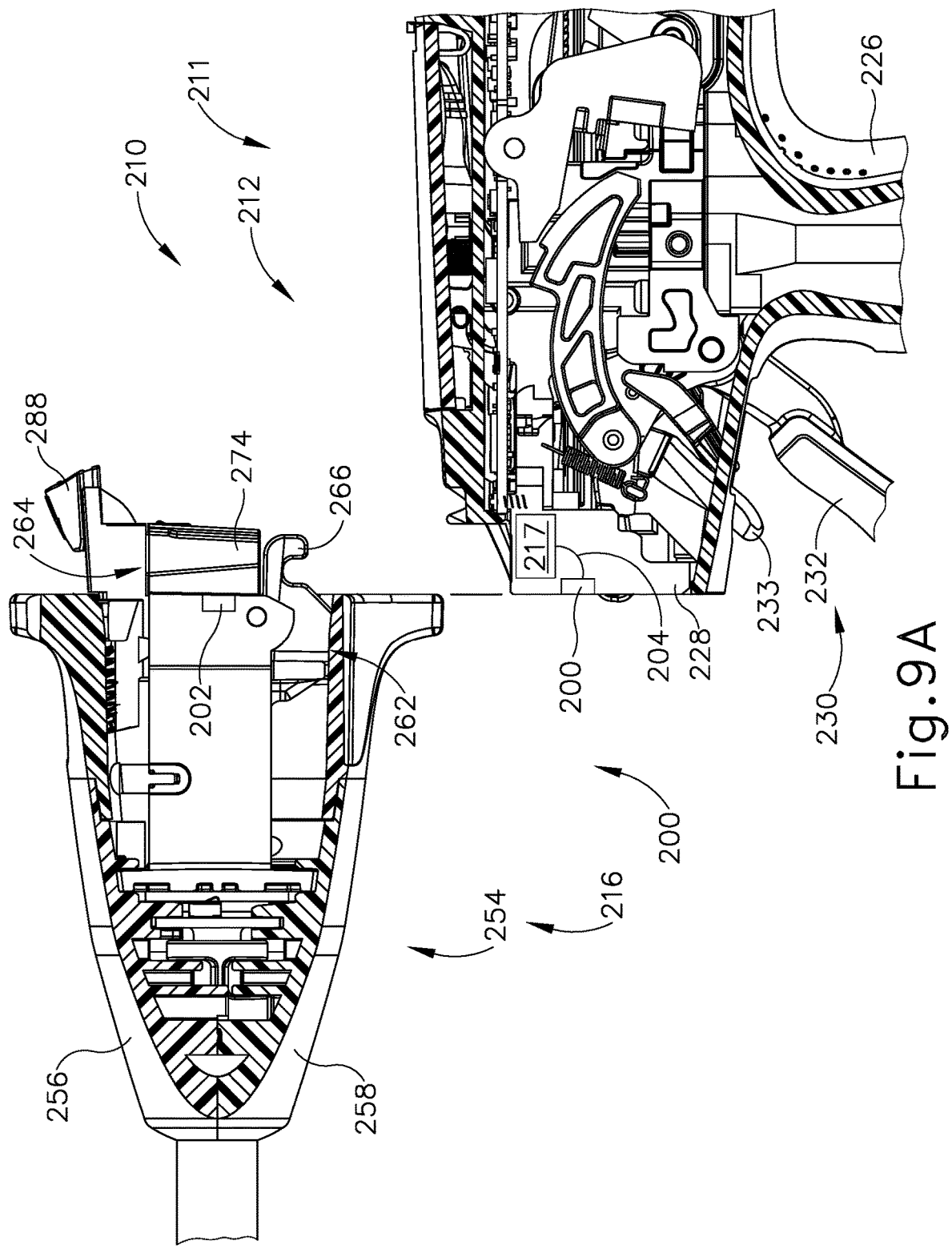
FIG. 9A depicts a cross-sectional side view of the handle assembly taken along line 9-9 of FIG. 7 and the shaft assembly of FIG. 8, where the shaft assembly is disassembled from the handle assembly.
Figure 9B:
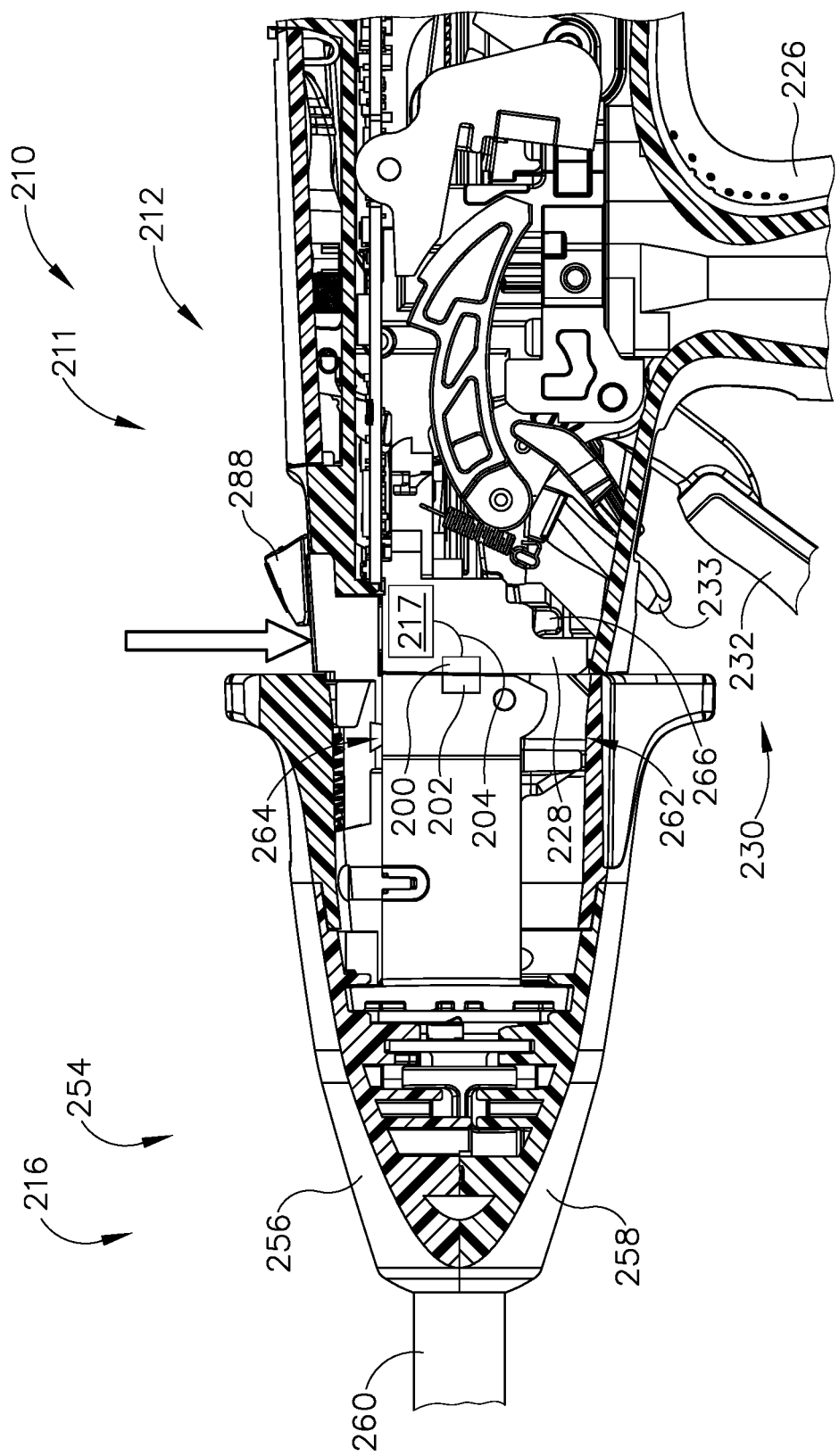
FIG. 9B depicts a cross-sectional side view of the handle assembly taken along line 9-9 of FIG. 7 and the shaft assembly of FIG. 8, where the shaft assembly is assembled with the handle assembly.

Control circuit (217) is substantially similar to control circuit (117) described above, with differences described below. As best seen in FIGS. 9A-9B, control circuit (217) is in communication with proximity sensors (200) via electrical connection (204). When proximity sensors (200) detect proximity targets (202) once handle assembly (211) and shaft assembly (216) are operatively engaged, proximity sensors (200) may communicate this detection to control circuit (217) of handle assembly (211) to complete the first step of the two-step verification process. It should be understood when only the first step of the two-step verification process is completed, control circuit (217) will not fully energize electrical connector (292).

Once proximity sensors (200) communicate detection of proximity targets (202) to control circuit (217), control circuit (217) may further verify proper coupling between handle assembly (211) and shaft assembly (216) through electrical connectors (290, 292). For example, control circuit (217) may briefly energize electrical connector (292) in an attempt to establish communication between control circuit (217) and shaft circuit board (219) via electrical connectors (290, 292). Any suitable type of information may be exchanged between control circuit (217) and shaft circuit board (219), as would be apparent to one having ordinary skill in the art in view of the teachings herein, in order to verify that handle assembly (211) and shaft assembly (216) are operatively engaged. In this example, if control circuit (217) establishes communication with shaft circuit board (218) via electrical connectors (290, 292), the second step in the two-step verification process is completed. Therefore, control circuit (217) may fully energize electrical connector (292) in order to operatively engage control circuit (217) with shaft assembly (216).

However, if the second step in the two-step verification process is not properly completed, control circuit (217) may not fully energize electrical connector (292). Additionally, control circuit (217) may instruct graphical user interface (218) to display an appropriate error signal, indicating to an operator that handle assembly (211) and shaft assembly (216) are not properly coupled, and therefore control circuit (217) is not fully energizing electrical connector (292).

While the exemplary second step in the two-step verification process described above includes an active step of control circuit (217) briefly attempting to establish communication between shaft circuit board (219) and control circuit (217), this is merely optional. For instance, the second step in the two-step verification process may involve a passive monitoring step that does not briefly energize electrical connector (292), but instead involves control circuit (217) passively measuring characteristics of an electrical circuit that should be formed by the coupling of electrical connectors (290, 292).

Once control circuit (217) receives a signal from proximity sensor (200) that proximity target (202) is detected, thereby completing the first step of the two-step verification process, control circuit (217) may attempt to validate the connection of contacts between electrical connectors (290, 292) through passive monitoring. The passive monitoring process may involve control circuit (217) measuring any suitable variable or combination of variables of an electrical circuit formed by the coupling of electrical connectors (290, 292). Variables that control circuit (217) may measure may include impedance or resistance, or any other suitable variable or combination of variables that would be known to a person having ordinary skill in the art in view of the teachings herein.

If the passively measured characteristic of the electrical circuit measured by control circuit (217) falls within a predetermined range associated with the proper coupling of electrical connectors (290, 292), control circuit (217) may assume handle assembly (211) and shaft assembly (216) are properly coupled, and therefore fully energize electrical connector (292). If the passively measured characteristic measured by control circuit (217) does not fall within the predetermined range associated with the proper coupling or electrical connectors (290, 292), control circuit (217) may not fully energy electrical connector (292). Additionally, control circuit (217) may instruct graphical user interface (218) to display an appropriate error signal, indicating to an operator that handle assembly (211) and shaft assembly (216) are not properly coupled such that control circuit (217) is not fully energizing electrical connector (292)

FIGS. 9A-9B show an exemplary coupling process between handle assembly (211) and shaft assembly (216). As shown in FIG. 9A, a clinician may place shaft assembly (216) above handle assembly (211) such that tapered attachment portions (274) of chassis (264) are aligned with and above dovetail slots (276) of flange portion (278) of frame (228). It should be understood at this point, proximity targets (202) are not close enough to be detected by proximity sensors (200). Therefore, proximity sensors (200) have not yet communicated detection of proximity targets (202) to control circuit (217). Because control circuit (217) has not received information from proximity sensors (200) corresponding to detections of proximity targets (202), control circuit (217) has yet to complete the first step of the two-step verification process, and therefore has yet to initiate the second step in the two-step verification process as described above. Electrical connection (292) is not capable of providing any electrical discharge when handle assembly (211) and shaft assembly (216) are in the position shown in FIG. 9A.

Next, as seen in FIG. 9B, a clinician may couple shaft assembly (216) and handle assembly (211) such that tapered attachment portions (274) of chassis (264) are within dovetail slots (276) of flange portion (278) of frame (228). At this point, shaft assembly (216) and handle assembly (211) may couple with each other in a similar fashion to shaft assembly (16) and handle assembly (11) described above. At this point, proximity targets (202) are close enough to be detected by proximity sensors (200) such that proximity sensors (200) may communicate detection of proximity targets (202) to control circuit (217). Therefore, the first step in the two-step verification process is completed. At this point, control circuit (217) may initiate the second step in the two-step verification process in accordance with the description above. If the second step in the two-step verification process is successful, control circuit (217) may fully activate electrical connector (292). If the second step in the two-step verification process is no successful, control circuit (217) may not fully activate electrical connector (292), and may further send an appropriate error signal to graphical user interface (218).

B. Exemplary Handle Assembly with Switch and Shaft Assembly with Contact Surface FIGS. 10-12B show another an exemplary motor driven surgical cutting and fastening instrument (310) including a handle assembly (311) and shaft assembly (316) that may confirm proper operative engagement between each other before fully energizing, as mentioned above. Handle assembly (311) is substantially similar to handle assembly (11) described above, with differences described below.

Handle assembly (311) includes a housing (312), a closure trigger (332), a firing trigger (333), a handle (314) including a pair of interconnectable handle housing segments (322, 324) cooperating to form a pistol grip portion (326), a battery pack (315), a frame (328) defining lock detents (398) and including a distal attachment flange portion (378) defining dovetail slots (376), a closure drive system (330), a closure linkage assembly (336), a second closure link (338), a transverse attachment pin (342), a closure release assembly (344) having a release button assembly (346), an articulation control rocker (320), a longitudinal driver member (386) forming a firing shaft attachment cradle (384), a control circuit (317), a graphical user interface (318), a home button (313), and an electrical connector (392); which are substantially similar to housing (12), closure trigger (32), firing trigger (33), handle (14) including a pair of interconnectable handle housing segments (22, 24) cooperating to form pistol grip portion (26), battery pack (110), frame (28) defining lock detents (98) and including distal attachment flange portion (78) defining dovetail slots (76), closure drive system (30), closure linkage assembly (36), second closure link (38), transverse attachment pin (42), closure release assembly (44) having release button assembly (46), articulation control rocker (112), longitudinal driver member (86) forming firing shaft attachment cradle (84), control circuit (117), graphical user interface (116), home button (114), and electrical connector (108) described above, respectively.

Shaft assembly (316) is substantially similar to shaft assembly (16) described above, with differences described below. Therefore, Shaft assembly (316) includes nozzle (354) including nozzle portions (356, 358), a closure tube (360), a closure shuttle (362) including a pair of proximally-protruding hooks (366), a chassis (364) including a pair of tapered attachment portions (374), an intermediate firing shaft (382) including a shaft attachment lug (380), a pair of proximally protruding lock lugs (396), a latch actuator assembly (388), and an electrical connector (390); which are substantially similar to nozzle (54) including nozzle portions (56, 58), closure tube (60), closure shuttle (62) including a pair of proximally-protruding hooks (66), chassis (64) including a pair of tapered attachment portions (74), intermediate firing shaft (82) including shaft attachment lug (80), a pair of proximally protruding lock lugs (96), latch actuator assembly (102), and electrical connector (106), described above, respectively. Shaft assembly (316) includes a shaft circuit board (319) in communication with electrical connector (390).

Shaft assembly (316) may be coupled to handle (314) in a similar fashion to how shaft assembly (16) couples with handle (14) described above. Therefore, when operatively engaged, five systems of interchangeable shaft assembly (316) may be operatively engaged with at least five corresponding systems of handle (314), similar to shaft assembly (16) and handle (14) described above. However, any suitable number of systems of interchangeability between shaft assembly (316) and handle (314) may be incorporated as would be apparent to one having ordinary skill in the art in view of the teachings herein.

Battery pack (315) is operable to selectively power control circuit (317), while control circuit (317) is in communication with electrical connector (392). Additionally, shaft circuit board (319) is in communication with electrical connector (390). When shaft assembly (316) and handle (314) are operatively engaged with each other, control circuit (317) and shaft circuit board (319) are in electrical communication via electrical connectors (392, 390).

Shaft assembly (316) may be coupled to any suitable type of end effector as would be apparent to one having ordinary skill in the art in view of the teachings herein. For instance, shaft assembly (316) may be operatively engaged to any end effector (18, 122, 132, 142) described above.

Figure 10:
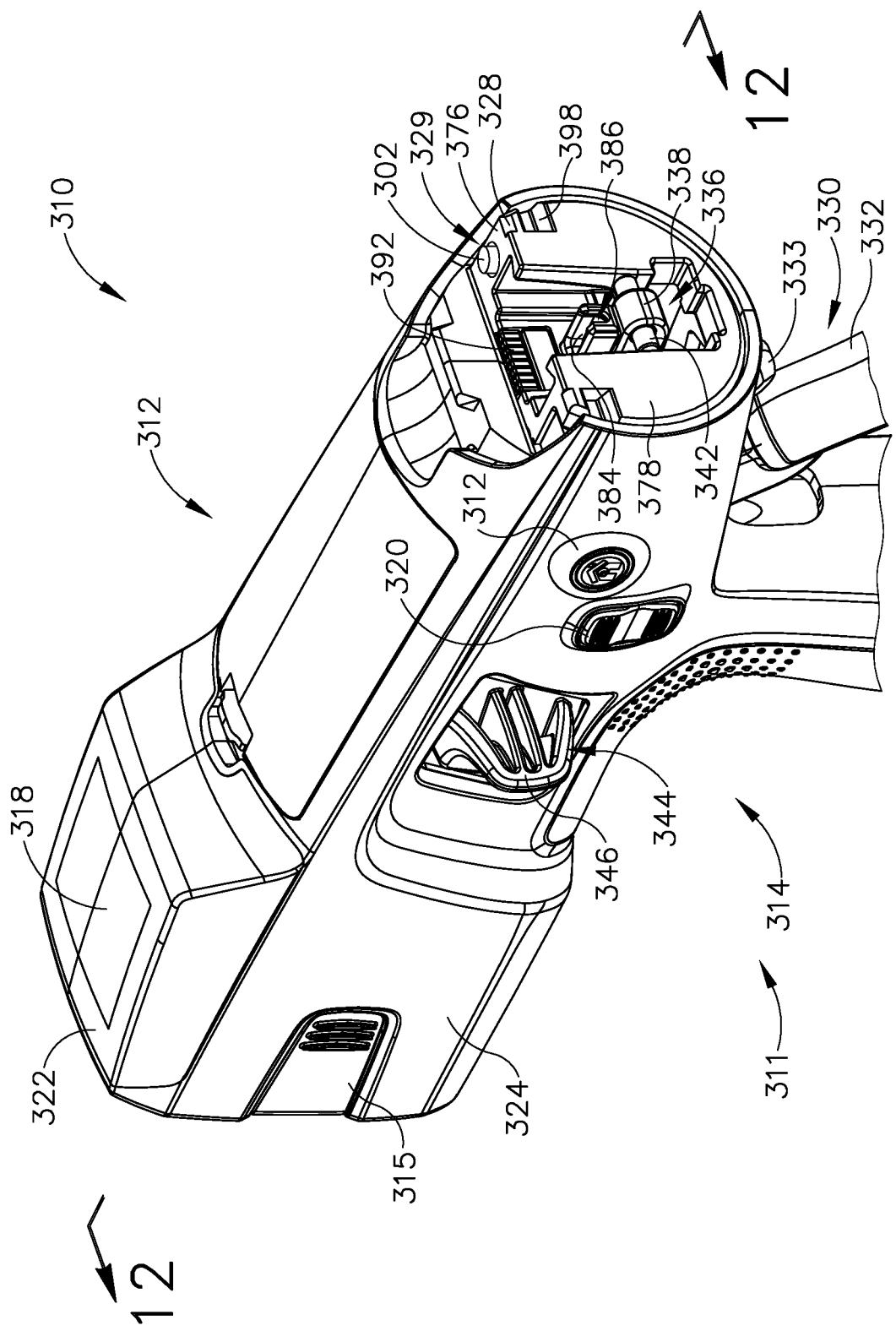
FIG. 10 depicts a perspective view of another exemplary alternative handle assembly that may be incorporated into the instrument of FIG. 1.
Figure 11:
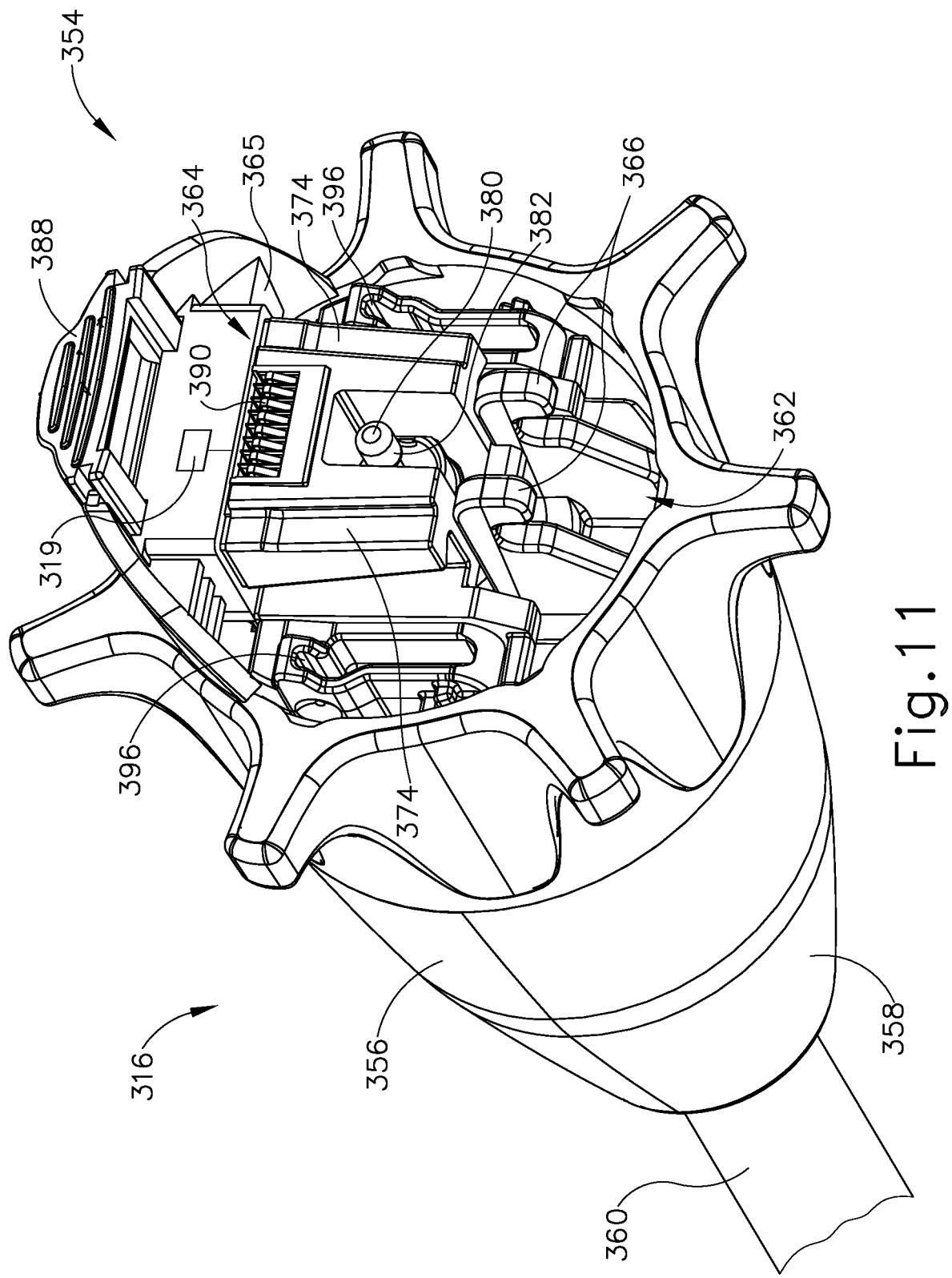
FIG. 11 depicts a perspective view of another exemplary alternative shaft assembly that may be assembled with the handle assembly of FIG. 10 to form another variation of the instrument of FIG. 1.
Figure 12A:
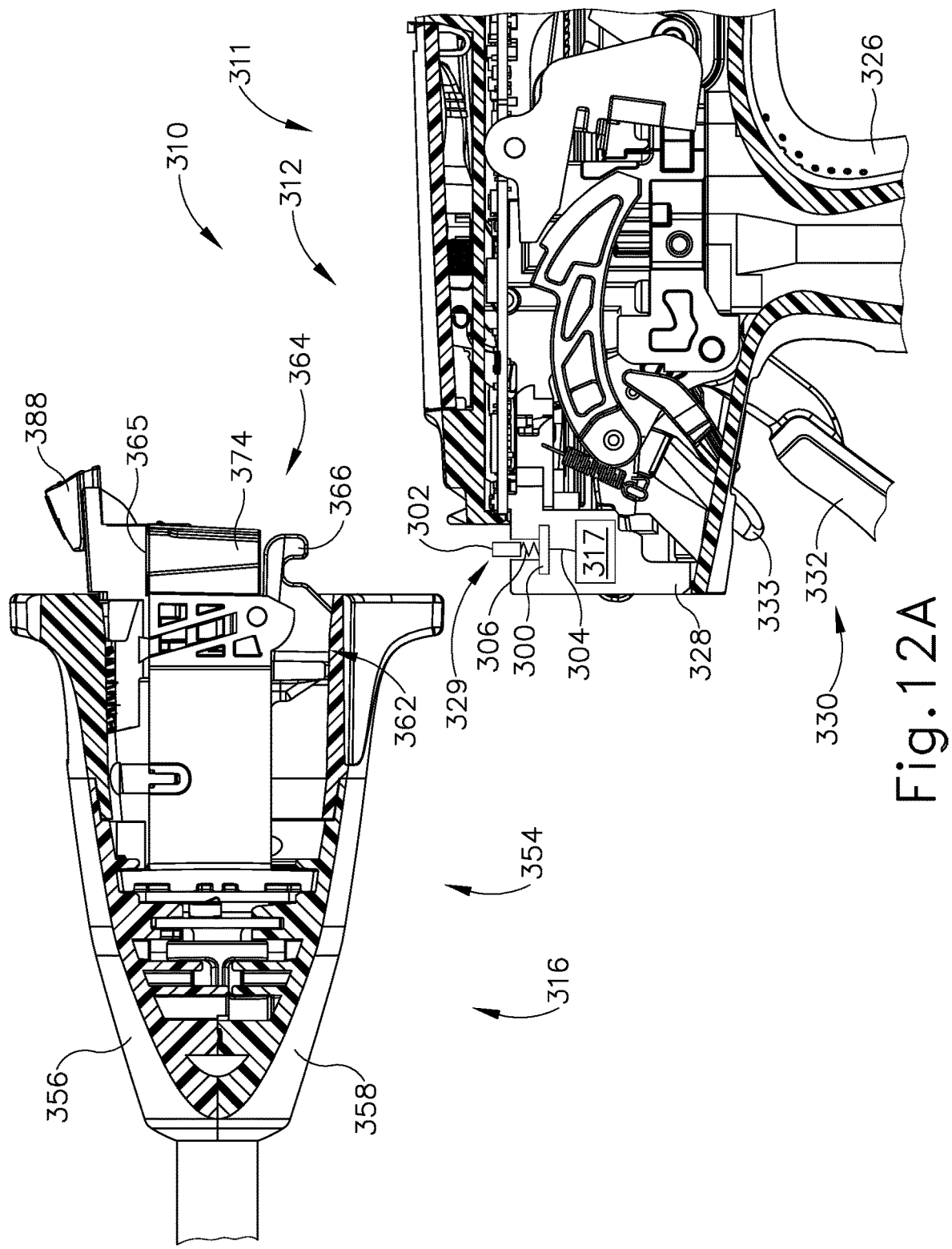
FIG. 12A depicts a cross-sectional side view of the handle assembly taken along line 12-12 of FIG. 10 and the shaft assembly of FIG. 11, where the shaft assembly is disassembled from the handle assembly.
Figure 12B:
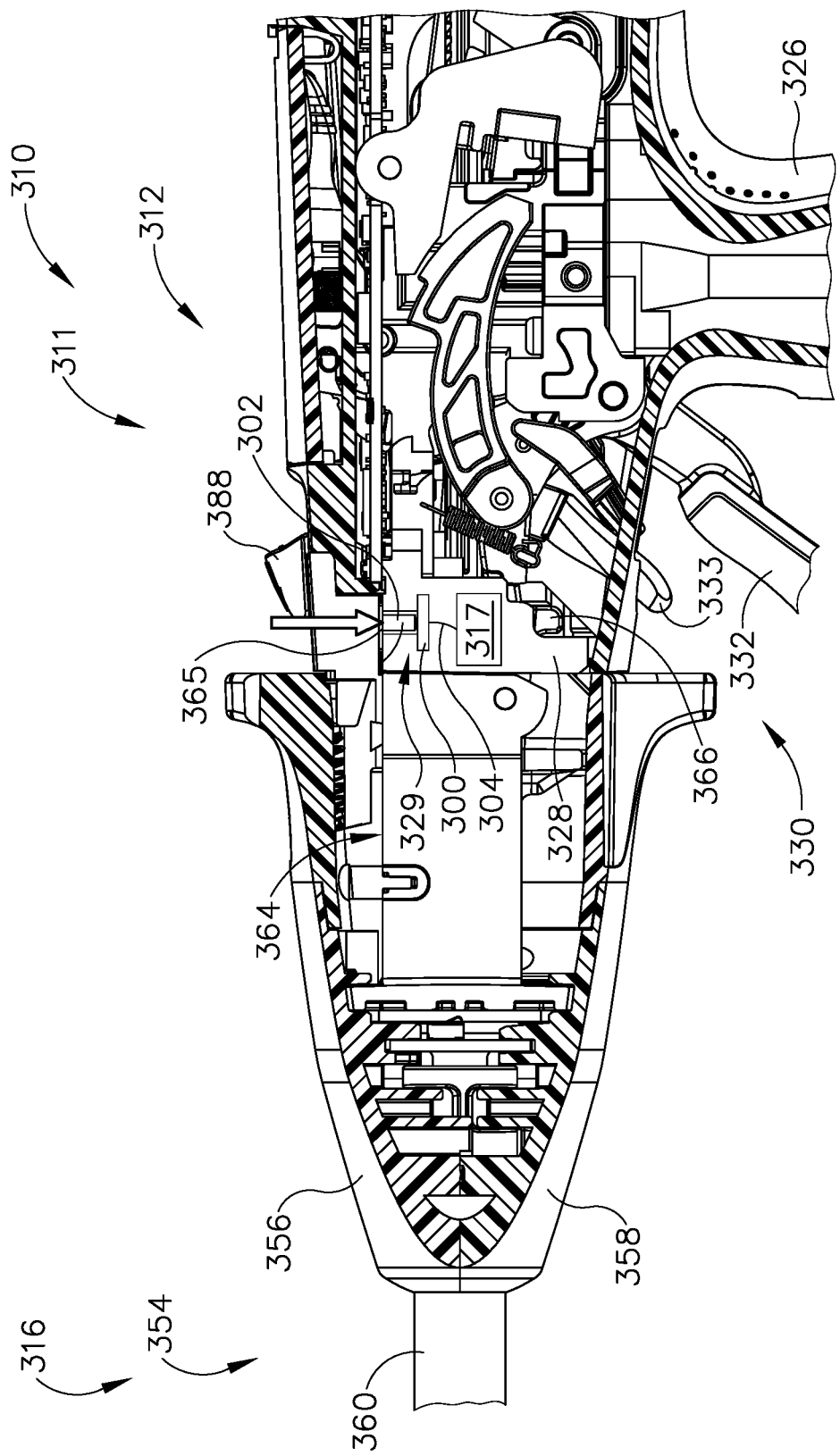
FIG. 12B depicts a cross-sectional side view of the handle assembly taken along line 12-12 of FIG. 10 and the shaft assembly of FIG. 11, where the shaft assembly is assembled with the handle assembly.

Additionally, as can be seen in FIG. 10, handle assembly (311) includes a button (302) housed within a recess (329) defined by frame (328). Shaft assembly (316) includes a contact surface (365). As best seen in FIG. 12A, button (302) is resiliently biased away from a switch (300) at a first position via a bias member (306) (e.g., a coil spring, etc.). As best seen in FIG. 12B, contact surface (365) may actuate button (302) when handle assembly (311) and shaft assembly (316) are operatively engaged. Interaction between contact surface (365) and button (302) overcomes the bias force of bias member (306) to actuate button (302) to a second position relative to frame (328) (as shown in FIG. 12B). In other words, when handle assembly (311) and shaft assembly (316) are operatively engaged, button (302) is actuated to the second position as shown in FIG. 12B. Button (302) is configured to activate switch (300) when button (302) is in the second position.

While in the current example, a portion of button (302) extends past frame (328) in the first position shown in FIG. 12A, this is merely optional. Alternatively, button (302) may entirely housed within frame (328) while in the first position. Therefore, contact surface (365) may be dimensioned with be inserted within recess (329) of frame (328) to actuate button (302) when handle assembly (311) and shaft assembly (316) are operatively engaged. Additionally, while switch (300) is configured to be activated by movement of button (302), switch (300) may be activated by any other suitable interaction between suitable components of handle assembly (311) and shaft assembly (316) that would be apparent to one having ordinary skill in the art in view of the teachings herein. For example, switch (300) may be configured to be activated by movement of second closure link (338) in response to second closure link (338) operatively connecting with proximally protruding hooks (366).

Control circuit (317) is substantially similar to control circuit (117) described above, with differences described below. As best seen in FIGS. 12A-12B, control circuit (317) is in communication with switch (300) via electrical connection (304). When switch (300) is activated by button (302) actuating to the second position in response to interaction with contact surface (302), switch (300) may communicate this detection to control circuit (317) of handle assembly (311) to complete the first step of the two-step verification process. It should be understood that button (302) may actuate to the second position in response to handle assembly (311) and shaft assembly (316) being operatively engaged to each other. It should also be understood when only the first step of the two-step verification process is completed, control circuit (317) will not fully energize electrical connector (392).

Once switch (300) communicates activation to control circuit (317) via actuation of button (302) to the second position, control circuit (317) may further verify proper coupling between handle assembly (311) and shaft assembly (316) through electrical connectors (390, 392). For example, control circuit (317) may briefly energize electrical connector (392) in an attempt to establish communication between control circuit (317) and shaft circuit board (319) via electrical connectors (390, 392). Any suitable type of information may be exchanged between control circuit (317) and shaft circuit board (319), as would be apparent to one having ordinary skill in the art in view of the teachings herein, in order to verify that handle assembly (311) and shaft assembly (316) are operatively engaged. In this example, if control circuit (317) establishes communication with shaft circuit board (318) via electrical connectors (390, 392), the second step in the two-step verification process is completed. Therefore, control circuit (317) may fully energize electrical connector (392) in order to operatively engage control circuit (317) with shaft assembly (316).

However, if the second step in the two-step verification process is not properly completed, control circuit (317) may not fully energize electrical connector (392). Additionally, control circuit (317) may instruct graphical user interface (318) to display an appropriate error signal, indicating to an operator that handle assembly (311) and shaft assembly (316) are not properly coupled, and therefore control circuit (317) is not fully energizing electrical connector (392).

While the exemplary second step in the two-step verification process described above includes an active step of control circuit (317) briefly attempting to establish communication between shaft circuit board (319) and control circuit (317), this is merely optional. For instance, the second step in the two-step verification process may involve a passive monitoring step that does not briefly energize electrical connector (392), but instead involves control circuit (317) passively measuring characteristics of an electrical circuit that should be formed by the proper coupling of electrical connectors (390, 392).

Once control circuit (317) receives a signal from switch (300) that button (302) is in the second position, thereby completing the first step of the two-step verification process, control circuit (317) may attempt to validate the connection of contacts between electrical connectors (390, 392) through passive monitoring. The passive monitoring process may involve control circuit (317) measuring any suitable variable or combination of variables of an electrical circuit formed by the coupling of electrical connectors (390, 392). Variables which control circuit (317) may measure may include impedance or resistance, or any other suitable variable/combination of variables that would be known to a person having ordinary skill in the art in view of the teachings herein.

If the passively measured characteristic of the electrical circuit measured by control circuit (317) falls within a predetermined range associated with the proper coupling of electrical connectors (390, 392), control circuit (317) may assume handle assembly (311) and shaft assembly (316) are properly coupled, and therefore fully energize electrical connector (392). If the passively measured characteristic measured by control circuit (317) does not fall within the predetermined range associated with the proper coupling or electrical connectors (390, 392), control circuit (317) may not fully energy electrical connector (392). Additionally, control circuit (317) may instruct graphical user interface (318) to display an appropriate error signal, indicating to an operator that handle assembly (311) and shaft assembly (316) are not properly coupled such that control circuit (317) is in not capable of fully energizing electrical connector (392).

FIGS. 12A-12B show an exemplary coupling process between handle assembly (311) and shaft assembly (316). As shown in FIG. 12A, a clinician may place shaft assembly (316) above handle assembly (311) such that tapered attachment portions (374) of chassis (364) are aligned with and above dovetail slots (376) of flange portion (378) of frame (328). It should be understood at this point, button (302) is in the first position due to biasing force provided by bias member (306). Therefore switch (300) has not activated and has not communicated this activation to control circuit (317). Because control circuit (317) has not received information from switch (300) corresponding to button (302) actuating to the second position, control circuit (317) has yet to complete the first step in the two-step verification process, and therefore has yet to initiate the second step in the two-step verification process as described above. Electrical connection (392) is not capable of providing any electrical discharge when handle assembly (311) and shaft assembly (316) are in the position shown in FIG. 12A.

Next, as seen in FIG. 12B, a clinician may couple shaft assembly (316) and handle assembly (311) such that tapered attachment portions (374) of chassis (364) are within dovetail slots (376) of flange portion (378) of frame (328). At this point, shaft assembly (316) and handle assembly (311) may couple with each other in a similar fashion to shaft assembly (16) and handle assembly (11) described above. Also at this point, button (302) is in the second position such that switch (200) may communicate activation of switch (200) to control circuit (317). Therefore, the first step in the two-step verification process is completed. At this point, control circuit (317) may initiate the second step in the two-step verification process in accordance with the description above. If the second step in the two-step verification process is successful, control circuit (317) may fully activate electrical connector (392). If the second step in the two-step verification process is no successful, control circuit (317) may not fully activate electrical connector (392), and may further send an appropriate error signal to graphical user interface (318).

C. Exemplary Electrical Connectors for Passive Detection

As mentioned above, the second step in the two-step verification process may involve a passive step where control circuit (217, 317) measures characteristics of an electrical circuit that should be formed by the coupling of electrical connectors (290, 292, 390, 392). In some instances, it may be desirable to have an electrical connector (290, 390) of shaft assembly (216, 316) configured to purposely provide an electrical short circuit between selected contacts when operatively engaged with electrical connector (292, 392) of handle assembly (214, 314).

Purposely providing an electrical short circuit between selected contacts may allow control circuit (217, 317) to more easily measure selected characteristics of an electrical circuit that should be formed by the coupling of electrical connectors (290, 292, 390, 392). Additionally and/or alternatively, if handle assembly (214, 316) is configured to couple with multiple shaft assemblies (216, 316) that provide multiple end effectors (18, 122, 132, 142), the passive characteristic measured may vary depending on which end effector (18, 122, 132, 142) is used. Therefore, providing an electrical short circuit between selected contacts may allow control circuit (217, 317) to uniformly measure characteristics of an electrical circuit formed by the coupling of electrical connectors (290, 292, 390, 392), regardless of which end effectors (18, 122, 132, 142) shaft assembly (216, 316) is attached.

Figure 13:
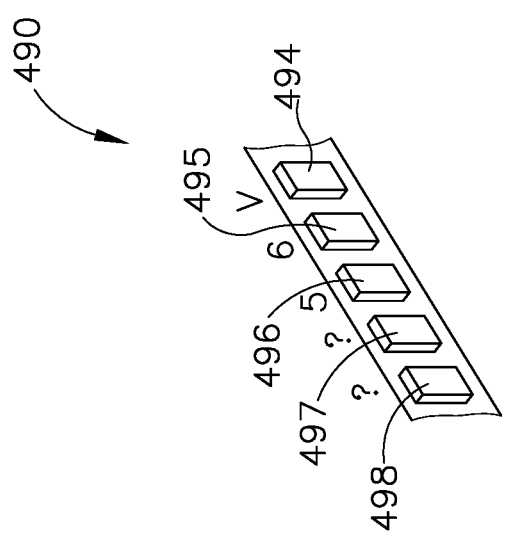
FIG. 13 depicts a perspective view of an exemplary alternative electrical connector that may be readily incorporated into the handle assembly of FIG. 1, FIG. 7, or FIG. 10.

FIG. 13 shows an alternative electrical connector (490) that may be readily incorporated into handle assembly (214, 314) described above in replacement of electrical connector (292, 392). Electrical connector (490) includes a plurality of electrical contacts (494, 495, 496, 497, 498). Each electrical contact (494, 495, 496, 497, 498) may be in communication with control circuit (217, 317) such that electrical contacts (494, 495, 496, 497, 498) are configured to contact one or multiple corresponding electrical contacts of shaft assembly (216, 316) to form electrical circuits. While the current example has five electrical contacts, any suitable number of contacts may be utilized as would be apparent to one having ordinary skill in the art in view of the teachings herein.

Figure 14:
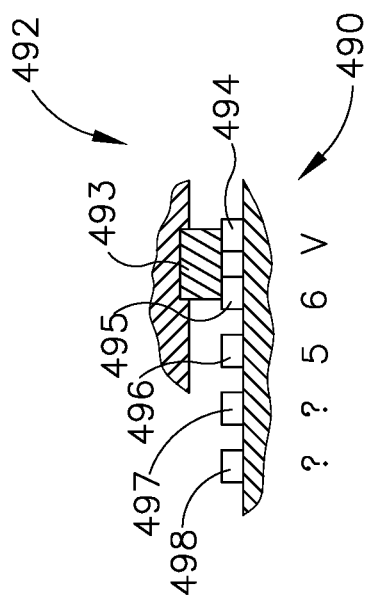
FIG. 14 depicts the electrical connector of FIG. 13 coupled with another exemplary alternative electrical connector that may readily incorporated into the shaft assembly of FIG. 1, FIG. 8, or FIG. 11.

FIG. 14 shows a portion of an alternative electrical connector (492) operatively coupled with electrical connector (490) described above. Electrical connector (492) may be readily incorporated into shaft assembly (216, 316) described above in replacement of electrical connectors (290, 390). Electrical connector (492) includes a short electrical contact (493). Short electrical contact (493) is not in communication with shaft circuit board (219, 319) described above, but instead directly connects electrical contacts (494, 495) to form a predetermined short circuit. Short electrical contact (493) thereby acts as a jumper between electrical contacts (494, 495), similar to just a wire, providing minimal resistance to newly formed electrical circuit between electrical contacts (494, 495) of electrical connector (492) and short electrical contact (493) of electrical connector (492). Therefore, when completing the second step in the two-step verification process as described above, control circuit (217, 317) may verify operative engagement between handle assembly (211, 311) and shaft assembly (216, 316) by measuring the resistance of the electrical circuit formed between electrical contacts (494, 493, 495) as approximately 0 ohms.

Figure 15:
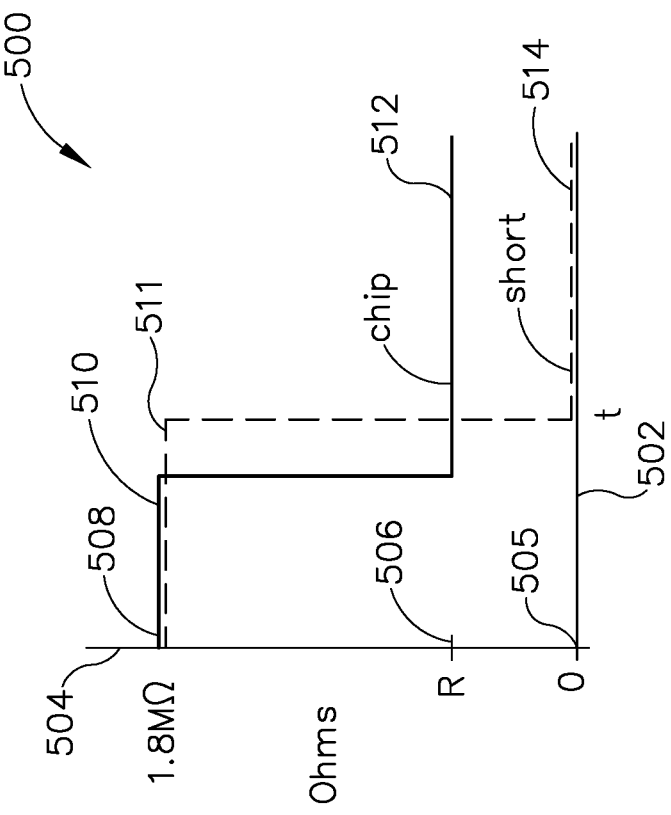
FIG. 15 depicts a line graph plotting resistance in an electrical circuit formed between two contacts of the electrical connectors of FIG. 14, and a line graph plotting resistance in an electrical circuit formed between the electrical connectors of the interchangeable shaft assembly of FIG. 1 and the handle assembly of FIG. 1 when operably connected.

FIG. 15 shows as exemplary line graph (500) of control circuit (217, 317) measuring resistance (504) as a function of time (502) between electrical contacts (494, 495), as shown in a dotted line; and control circuit (217, 317) measuring resistance (504) as a function of time (502) between selected electrical contacts of electrical connector (292, 392), as shown in a solid line.

At first, resistance measured (511, 510) between electrical contacts (494, 495) and between selected electrical contacts of electrical connector (292, 392) are 1.8 megaohms (508) (e.g., essentially infinite resistance) when shaft assembly (216, 316) is not operatively engaged with handle assembly (211, 311). This resistance measured by control circuit (217, 317) is associated with an open circuit, since shaft assembly (216, 316) is not operatively engaged with handle assembly (211, 311).

Next, handle assembly (211, 311) and shaft assembly (216, 316) may be operatively engaged with each other such that either electrical contacts (494, 495) are connected by short electrical contact (493), or such that selected electrical contacts of electrical connector (290, 390) are connected with selected electrical contacts of electrical connector (292, 392). At this point, in instances where electrical connectors (490, 492) are used, and handle assembly (211, 311) and shaft assembly (216, 316) are operatively engaged, resistance measured (514) between electrical contacts (494, 495) is substantially 0 ohms (505) due to short electrical contact (493) directly connecting electrical contacts (492, 495) without adding any meaningful resistance. If control circuit (217, 317) measures the resistance formed by electrical contacts (493, 493, 495) within a predetermined range of 0 ohms (505), control circuit (217, 317) may have verified the second step in the two-step verification process and fully activated electrical connectors (490).

At this point, in instances where electrical connectors (290, 292, 390, 392) are used, and when handle assembly (211, 311) and shaft assembly (216, 316) are operatively engaged, selected electrical contacts in electrical connectors (290, 292, 390, 392) form an electrical circuit with a resistance measured (512) of R ohms (506). If control circuit (217, 317) measures the resistance formed by selected electrical contacts within a predetermined range of R ohms (506), control circuit (217, 317) may have verified the second step in the two-step verification process and then fully activate electrical connector (292, 392).

D. Exemplary Verification Process

Figure 16:
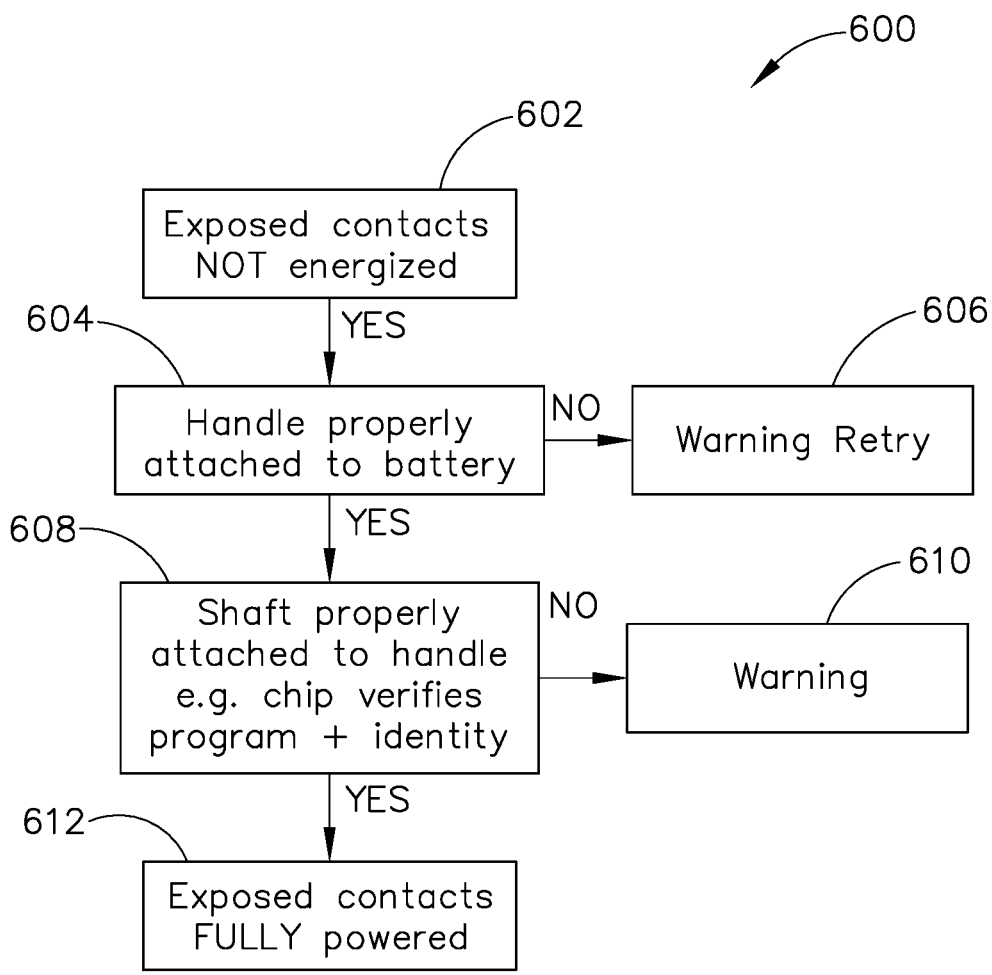
FIG. 16 depicts a flow chart of an exemplary method that may be performed when coupling the shaft assembly of FIG. 8 or FIG. 11 with the handle assembly of FIG. 7 or FIG. 10, respectively.

FIG. 16 shows an exemplary verification process (600) that motor driven surgical cutting and fastening instrument (210, 310) may use. First, control circuit (217, 317) may confirm that exposed contacts (292, 392) of handle assembly (211, 311) are not energized (602). Next, control circuit (217, 317) may determine whether or not handle assembly (211, 311) is properly attached (604) to battery pack (215, 315). If handle assembly (211, 311) is not properly attached (604) to battery pack (215, 315), control circuit (217, 317) may instruct graphical user interface (218, 318) to display a warning message and to retry (606). If control circuit (217, 317) determined handle assembly (211, 311) is properly attached (504) to battery pack (215, 315), control circuit (217, 317) may now be prepared to initiate the two-step verification process (608), as described above. If the two-step verification process is not properly completed, control circuit (217, 317) may instruct graphical user interface (218, 318) to display a warning/error message (610). If the two-step verification process is properly completed, control circuit (217, 317) my fully energize (612) electrical contacts (292, 392) of handle assembly (211, 311).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a body assembly, wherein the body assembly comprises: (i) a control circuit, (ii) a battery pack operable to power the control circuit, and (iii) a first electrical contact assembly, wherein the first electrical contact assembly is in communication with the control circuit; (b) a modular shaft assembly configured to selectively couple with the body assembly, wherein the modular shaft assembly comprises a second electrical contact assembly, wherein the second electrical contact assembly is configured to operatively engage the first electrical contact assembly when the modular shaft assembly selectively couples with the body assembly; and (c) a coupling detection assembly comprising: (i) a detection activation member associated with the body assembly, wherein the detection activation member is in communication with the control circuit, and (ii) a detection trigger member associated with the modular shaft assembly, wherein the detection trigger member is configured to activate the detection activation member such that the detection activation member communicates a first detection signal to the control circuit when the modular shaft assembly selectively couples with the body assembly; wherein the control circuit is configured to verify operative engagement between the first electrical contact and the second electrical contact in response to the control circuit receiving the first detection signal, wherein the control circuit is configured to energize the first electrical contact in response to verifying operative engagement between the first electrical contact and the second electrical contact.

Example 2

The apparatus of Example 1, wherein the detection activation member comprises a proximity target, wherein the detection trigger member comprises a proximity sensor configured to detect the proximity target when the modular shaft assembly is operatively engaged with body assembly.

Example 3

The apparatus of Example 2, wherein the proximity target comprises a magnet, wherein the proximity sensor comprises a Hall effect sensor.

Example 4

The apparatus of any one or more of Examples 1 through 3, wherein the detection activation member comprises a button and a switch, wherein the switch is in communication with the control circuit, wherein the button is configured actuate from a first position to a second position to activate the switch to selectively communicate the first detection signal to the control circuit when the modular shaft assembly is operatively engaged with the body assembly.

Example 5

The apparatus of Example 4, wherein the button is resiliently biased to the first position.

Example 6

The apparatus of any one or more of Examples 4 through 5, wherein the body assembly further comprises a frame, wherein the switch is fixed relative to the frame.

Example 7

The apparatus of Example 6, wherein the button is slidably housed within the frame of the body assembly.

Example 8

The apparatus of any one or more of Examples 1 through 7, wherein the modular shaft assembly comprises a circuit board, wherein the circuit board is in communication with the second electrical contact of the modular shaft assembly.

Example 9

The apparatus of Example 8, wherein the control circuit is configured to briefly energize the first electrical contact to establish communication with the circuit board to verify operative engagement between the first electrical contact and the second electrical contact.

Example 10

The apparatus of any one or more of Examples 8 through 9, wherein the control circuit is configured to measure an electrical impedance of an electrical circuit formed between the first electrical contact and the second electrical contact to verify operative engagement between the first electrical contact and the second electrical contact.

Example 11

The apparatus of any one or more of Examples 8 through 10, wherein the control circuit is configured to measure an electrical resistance of an electrical circuit formed between the first electrical contact and the second electrical contact to verify operative engagement between the first electrical contact and the second electrical contact.

Example 12 apparatus of Example 11, wherein the second electrical contact comprise a short circuit connector configured to couple with the first electrical contact to force the resistance of the electrical circuit to be substantially zero ohms.

Example 13

The apparatus of any one or more of Examples 1 through 12, wherein the body assembly further comprises an indicator in communication with the control circuit, wherein the control circuit is configured to activate the indicator if the control circuit does not verify operative engagement between the first electrical contact and the second electrical contact.

Example 14

The apparatus of any one or more of Examples 1 through 13, wherein the module shaft assembly comprises an end effector.

Example 15

The apparatus of Example 14, wherein the end effector comprises a lower jaw and an anvil.

Example 16

The apparatus of Example 14, wherein the end effector comprises a circular stapling head assembly.

Example 17

An apparatus, comprising: (a) a body assembly, wherein the body assembly comprises: (i) a control circuit, and (ii) a first electrical contact assembly, wherein the first electrical contact assembly is in communication with the control circuit; (b) a modular shaft assembly configured to selectively couple with the body assembly, wherein the modular shaft assembly comprises: (i) a circuit board, and (ii) a second electrical contact assembly in communication with the circuit board, wherein the second electrical contact assembly is configured to operatively engage the first electrical contact assembly when the modular shaft assembly is selectively coupled to the body assembly; and (c) a coupling detection assembly comprising: (i) a detection activation member associated with the body assembly, wherein the detection activation member is in communication with the control circuit, and (ii) a detection trigger member associated with the modular shaft assembly, wherein the detection trigger member is configured to activate the detection activation member such that the detection activation member communicates a first detection signal to the control circuit when the modular shaft assembly selectively couples with the body assembly; wherein the control circuit is configured to verify operative engagement between the control circuit and the circuit board in response to receiving the first detection signal, wherein the control circuit is configured to energize the first electrical contact in response to verifying operative engagement between the control circuit and the circuit board.

Example 18

The apparatus of Example 17, wherein the control circuit is configured to verify operative engagement between the control circuit and the circuit board via a passive monitoring step.

Example 19

An apparatus, comprising: (a) a body assembly, wherein the body assembly comprises: (i) a control circuit, and (iii) a first electrical contact assembly, wherein the control circuit is configured to fully activate the first electrical contact; (b) a modular shaft assembly configured to selectively couple with the body assembly, wherein the modular shaft assembly comprises a second electrical contact assembly, wherein the second electrical contact assembly is configured to operatively engage the first electrical contact assembly when the modular shaft assembly selectively couples with the body assembly; and (c) a coupling detection assembly comprising: (i) a detection activation member associated with the body assembly, wherein the detection activation member is in communication with the control circuit, and (ii) a detection trigger member associated with the modular shaft assembly, wherein the detection trigger member is configured to activate the detection activation member such that the detection activation member communicates a first detection signal to the control circuit when the modular shaft assembly selectively couples with the body assembly; wherein the control circuit is configured to verify connection between the first electrical contact assembly and the second electrical contact assembly in response to the first detection signal prior to fully activating the first electrical contact assembly.

Example 20

The apparatus of Example 19, wherein the modular shaft assembly defines a longitudinal axis, wherein the modular shaft assembly is configured to rotate about the longitudinal axis relative to the body assembly when the modular shaft assembly is selectively coupled with the body assembly.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent application Ser. No. 15/634,385, entitled "Apparatus and Method to Determine End of Life of Battery Powered Surgical Instrument," filed on Jun. 27, 2017, published as U.S. Pub. No. 2018/0368821 on Dec. 27, 2018, the disclosure of which is incorporated by reference herein. Various suitable ways in which the teachings herein may be combined with the teachings of U.S. patent application Ser. No. 15/634,385, filed on Jun. 27, 2017, published as U.S. Pub. 2018/0368821 on Dec. 27, 2018, will be apparent to those of ordinary skill in the art in view of the teachings herein.

In addition to the foregoing, the teachings herein may be readily combined with the teachings of U.S. patent application Ser. No. 15/634,418, entitled "Surgical Instrument with Integrated and Independently Powered Displays," filed on Jun. 27, 2017, issued as U.S. Pat. No. 10,163,309 on Dec. 25, 2018, the disclosure of which is incorporated by reference herein. Various suitable ways in which the teachings herein may be combined with the teachings of U.S. patent application Ser. No. 15/634,418 filed on Jun. 27, 2017, issued as U.S. Pat. No. 10,163,309 on Dec. 25, 2018, will be apparent to those of ordinary skill in the art in view of the teachings herein.

In addition to the foregoing, the teachings herein may be readily combined with the teachings of U.S. patent application Ser. No. 15/634,436, entitled "Battery Pack with Integrated Circuit Providing Sleep Mode to Battery Pack and Associated Surgical Instrument," filed on Jun. 27, 2017, published as U.S. Pub. No. 2018/0368822 on Dec. 27, 2018, the disclosure of which is incorporated by reference herein. Various suitable ways in which the teachings herein may be combined with the teachings of U.S. patent application Ser. No. 15/634,436 filed on Jun. 27, 2017, published as U.S. Pub. No. 2018/0368822 on Dec. 27, 2018, will be apparent to those of ordinary skill in the art in view of the teachings herein.

In addition to the foregoing, the teachings herein may be readily combined with the teachings of U.S. patent application Ser. No. 15/634,452, entitled "Battery Powered Surgical Instrument with Dual Power Utilization Circuits for Dual Modes," filed on Jun. 27, 2017, issued as U.S. Pat. No. 10,511,065 on Dec. 17, 2019, the disclosure of which is incorporated by reference herein. Various suitable ways in which the teachings herein may be combined with the teachings of U.S. patent application Ser. No. 15/634,452 filed on Jun. 27, 2017, issued as U.S. Pat. No. 10,511,065 on Dec. 17, 2019, will be apparent to those of ordinary skill in the art in view of the teachings herein.

In addition to the foregoing, the teachings herein may be readily combined with the teachings of U.S. patent application Ser. No. 15/634,475, entitled "Powered Surgical Instrument with Latching Feature Preventing Removal of Battery Pack," filed on Jun. 27, 2017, published as U.S. Pub. No. 2018/0368848 on Dec. 27, 2018, the disclosure of which is incorporated by reference herein. Various suitable ways in which the teachings herein may be combined with the teachings of U.S. patent application Ser. No. 15/634,475 filed on Jun. 27, 2017, published as U.S. Pub. No. 2018/

0368848 on Dec. 27, 2018, will be apparent to those of ordinary skill in the art in view of the teachings herein.

In addition to the foregoing, the teachings herein may be readily combined with the teachings of U.S. patent application Ser. No. 15/634,524, entitled "Powered Surgical Instrument with Independent Selectively Applied Rotary and Linear Drivetrains," filed on Jun. 27, 2017, published as U.S. Pub. No. 2018/0368850 on Dec. 27, 2018, the disclosure of which is incorporated by reference herein. Various suitable ways in which the teachings herein may be combined with the teachings of U.S. patent application Ser. No. 15/634,524 filed on Jun. 27, 2017, published as U.S. Pub. No. 2018/0368850 on Dec. 27, 2018, will be apparent to those of ordinary skill in the art in view of the teachings herein.

In addition to the foregoing, the teachings herein may be readily combined with the teachings of U.S. patent application Ser. No. 15/634,556, entitled "Powered Circular Stapler with Reciprocating Drive Member to Provide Independent Stapling and Cutting of Tissue," filed on Jun. 27, 2017, published as U.S. Pub. No. 2018/0368851 on Dec. 27, 2019, the disclosure of which is incorporated by reference herein. Various suitable ways in which the teachings herein may be combined with the teachings of U.S. patent application Ser. No. 15/634,556 filed on Jun. 27, 2017, published as U.S. Pub No. 2018/0368851 Dec. 27, 2019, will be apparent to those of ordinary skill in the art in view of the teachings herein.

In addition to the foregoing, the teachings herein may be readily combined with the teachings of U.S. patent application Ser. No. 15/634,620, entitled "Surgical Stapler with Independently Actuated Drivers to Provide Varying Staple Heights," filed on Jun. 27, 2017, published as U.S. Pub. No. 2018/0368836 on Dec. 27, 2018, the disclosure of which is incorporated by reference herein. Various suitable ways in which the teachings herein may be combined with the teachings of U.S. patent application Ser. No. 15/634,620 filed on Jun. 27, 2018, published as U.S. Pub. No. 2018/0368836 on Dec. 27, 2018, will be apparent to those of ordinary skill in the art in view of the teachings herein.

In addition to the foregoing, the teachings herein may be readily combined with the teachings of U.S. patent application Ser. No. 15/634,589, entitled "Surgical Instrument Handle Assembly with Feature to Clean Electrical Contacts at Modular Shaft Interface," filed on Jun. 27, 2017, issued as U.S. Pat. No. 10,090,616 on Oct. 2, 2018, the disclosure of which is incorporated by reference herein. Various suitable ways in which the teachings herein may be combined with the teachings of U.S. patent application Ser. No. 15/634,589 filed on Jun. 27, 2017, published as U.S. Pub. No. 10,090,616 on Oct. 2, 2018, will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a body assembly, wherein the body assembly comprises:

(i) a control circuit,
(ii) a battery pack operable to power the control circuit, and
(iii) a first electrical contact assembly, wherein the first electrical contact assembly is in communication with the control circuit;
(b) a modular shaft assembly configured to selectively couple with the body assembly, wherein the modular shaft assembly comprises a second electrical contact assembly, wherein the second electrical contact assembly is configured to operatively engage the first electrical contact assembly when the modular shaft assembly selectively couples with the body assembly; and
(c) a coupling detection assembly comprising:
(i) a detection activation member associated with the body assembly, wherein the detection activation member is in communication with the control circuit, and
(ii) a detection trigger member associated with the modular shaft assembly, wherein the detection trigger member is configured to activate the detection activation member such that the detection activation member communicates a first detection signal to the control circuit when the modular shaft assembly selectively couples with the body assembly;
wherein the control circuit is configured to verify operative engagement between the first electrical contact and the second electrical contact after and in response to the control circuit receiving the first detection signal,
wherein the control circuit is configured to fully activate the first electrical contact in response to the control circuit both receiving the first detection signal and then successfully verifying operative engagement between the first electrical contact and the second electrical contact.

2. The apparatus of claim 1, wherein the detection trigger member comprises a proximity target, wherein the detection activation member comprises a proximity sensor configured to detect the proximity target when the modular shaft assembly is operatively engaged with body assembly.

3. The apparatus of claim 2, wherein the proximity target comprises a magnet, wherein the proximity sensor comprises a Hall effect sensor.

4. The apparatus of claim 1, wherein the detection activation member comprises a button and a switch, wherein the switch is in communication with the control circuit, wherein the button is configured actuate from a first position to a second position to activate the switch to selectively communicate the first detection signal to the control circuit when the modular shaft assembly is operatively engaged with the body assembly.

5. The apparatus of claim 4, wherein the button is resiliently biased to the first position.

6. The apparatus of claim 4, wherein the body assembly further comprises a frame, wherein the switch is fixed relative to the frame.

7. The apparatus of claim 6, wherein the button is slidably housed within the frame of the body assembly.

8. The apparatus of claim 1, wherein the modular shaft assembly comprises a circuit board, wherein the circuit board is in communication with the second electrical contact of the modular shaft assembly.

9. The apparatus of claim 8, wherein the control circuit is configured to briefly energize the first electrical contact to establish communication with the circuit board to verify operative engagement between the first electrical contact and the second electrical contact.

10. The apparatus of claim 8, wherein the control circuit is configured to measure an electrical impedance of an electrical circuit formed between the first electrical contact and the second electrical contact to verify operative engagement between the first electrical contact and the second electrical contact.

11. The apparatus of claim 8, wherein the control circuit is configured to measure an electrical resistance of an electrical circuit formed between the first electrical contact and the second electrical contact to verify operative engagement between the first electrical contact and the second electrical contact.

12. The apparatus of claim 11, wherein the second electrical contact comprise a short circuit connector configured to couple with the first electrical contact to force the resistance of the electrical circuit to be substantially zero ohms.

13. The apparatus of claim 1, wherein the body assembly further comprises an indicator in communication with the control circuit, wherein the control circuit is configured to activate the indicator if the control circuit does not verify operative engagement between the first electrical contact and the second electrical contact.

14. The apparatus of claim 1, wherein the module shaft assembly comprises an end effector.

15. The apparatus of claim 14, wherein the end effector comprises a lower jaw and an anvil.

16. The apparatus of claim 14, wherein the end effector comprises a circular stapling head assembly.

17. An apparatus, comprising:
(a) a body assembly, wherein the body assembly comprises:
(i) a control circuit, and
(ii) a first electrical contact assembly, wherein the first electrical contact assembly is in communication with the control circuit;
(b) a modular shaft assembly configured to selectively couple with the body assembly, wherein the modular shaft assembly comprises:
(i) a circuit board, and
(ii) a second electrical contact assembly in communication with the circuit board, wherein the second electrical contact assembly is configured to operatively engage the first electrical contact assembly when the modular shaft assembly is selectively coupled to the body assembly; and
(c) a coupling detection assembly comprising:
(i) a detection activation member associated with the body assembly, wherein the detection activation member is in communication with the control circuit, and
(ii) a detection trigger member associated with the modular shaft assembly, wherein the detection trigger member is configured to activate the detection activation member such that the detection activation member communicates a first detection signal to the control circuit when the modular shaft assembly selectively couples with the body assembly;
wherein the control circuit is configured to verify operative engagement between the control circuit and the circuit board in response to receiving the first detection signal before the first electrical contact is fully energized for operative engagement with the second electrical contact,
wherein the control circuit is configured to fully energize the first electrical contact for operative engagement with the second electrical contact in response to receiving the first detection signal and successfully verifying operative engagement between the control circuit and the circuit board.

18. The apparatus of claim 17, wherein the control circuit is configured to verify operative engagement between the control circuit and the circuit board via a passive monitoring step.

19. An apparatus, comprising:
(a) a body assembly, wherein the body assembly comprises:
  (i) a control circuit, and
  (ii) a first electrical contact assembly comprising a first short contact assembly, wherein the control circuit is configured to fully activate the first electrical contact;
(b) a modular shaft assembly configured to selectively couple with the body assembly, wherein the modular shaft assembly comprises a second electrical contact assembly comprising a second short contact assembly, wherein the second electrical contact assembly is configured to operatively engage the first electrical contact assembly when the modular shaft assembly selectively couples with the body assembly, wherein the first short contact assembly and the second short contact assembly are configured to form a short electrical contact; and
(c) a coupling detection assembly comprising:
  (i) a detection activation member associated with the body assembly, wherein the detection activation member is in communication with the control circuit, and
  (ii) a detection trigger member associated with the modular shaft assembly, wherein the detection trigger member is configured to activate the detection activation member such that the detection activation member communicates a first detection signal to the control circuit when the modular shaft assembly selectively couples with the body assembly;
wherein the control circuit is configured to successfully verify connection between the first electrical contact assembly and the second electrical contact assembly by measuring a resistance in the short electrical contact after and in response to the control circuit receiving the first detection signal, wherein the control circuit is configured to fully activate the first electrical contact assembly in response to measuring the resistance in the short electrical contact.

20. The apparatus of claim 19, wherein the modular shaft assembly defines a longitudinal axis, wherein the modular shaft assembly is configured to rotate about the longitudinal axis relative to the body assembly when the modular shaft assembly is selectively coupled with the body assembly.

* * * * *